United States Patent [19]

Lichtenberger

[11] Patent Number: 5,260,284
[45] Date of Patent: Nov. 9, 1993

[54] METHODS EMPLOYING UNIQUE MIXTURES OF POLAR AND NEUTRAL LIPIDS AND STEROL FOR LUNG SURFACTANT REPLACEMENT THERAPY

[75] Inventor: Lenard M. Lichtenberger, Houston, Tex.

[73] Assignee: Board of Regents, The University of Texas System

[21] Appl. No.: 862,841

[22] Filed: Apr. 3, 1992

Related U.S. Application Data

[60] Division of Ser. No. 636,672, Feb. 4, 1992, Pat. No. 5,134,129, which is a division of Ser. No. 323,671, Mar. 15, 1989, Pat. No. 5,032,585, which is a continuation-in-part of Ser. No. 15,394, Feb. 17, 1987, Pat. No. 4,918,063.

[51] Int. Cl.$^5$ .................. A61K 31/685; A61K 31/56; A61K 31/20
[52] U.S. Cl. ..................... 514/78; 514/171; 514/558
[58] Field of Search .................. 514/77, 78, 171, 558

[56] References Cited

U.S. PATENT DOCUMENTS

| | | | |
|---|---|---|---|
| 4,287,174 | 9/1981 | Laughlin | 424/78 |
| 4,340,594 | 7/1982 | Mizushima et al. | 424/238 |
| 4,369,182 | 1/1983 | Ghyczy et al. | 424/199 |
| 4,542,019 | 9/1985 | Lezdey | 424/157 |

FOREIGN PATENT DOCUMENTS

| | | |
|---|---|---|
| 0074251a1 | 3/1983 | European Pat. Off. . |
| 0110498a1 | 6/1984 | European Pat. Off. . |
| 0213724 | 3/1987 | European Pat. Off. . |
| 092121 | 12/1987 | European Pat. Off. . |
| A2554592 | 6/1977 | Fed. Rep. of Germany . |
| 5060 M | 5/1967 | France . |
| 2445146 | 7/1980 | France . |
| 2002631 | 2/1979 | United Kingdom . |
| 2080324 | 2/1982 | United Kingdom . |

OTHER PUBLICATIONS

Merck Manual, 1987, pp. 480–482 Merck, Sharp & Dohme Research Lab. Pub.
European Search Report, in Related File Serial No. 015,394, EP 88 301336, Jul. 15, 1988.
Partial European Search Report, Application EP 83 10 3437.6 Jul. 19, 1983.
Horowitz et al. (1974), Changes in gastric mucosa lipid profile with development of stress ulcer in rats., Fed. Proc., 33(3): Abstract only.
Wassef et al. (1979), Molecular species of phosphatidylcholine from rat gastric mucosa., BBA Reports, 573:222.
Ikegami et al. (1980), Restoration of lung pressure–volume characteristics with various phospholipids., Chem. Abstracts, 92:62, Abstract No. 15574p 15567.
Duane et al. (1980), Mechanism by which Bile Salt Disrupts the Gastric Mucosal Barrier in the Dog., Jrnl. Clin. Inves., 66:1044.
Hills (1982), Water Repellency Induced by Pulmonary Surfactants., J. Physiol., 325:175.
Duane et al. (1982), Bile acid and bile salt disrupt gastric mucosal barrier in the dog by different mechanisms., Am. J. Physiol., 242:G95–G99.

(List continued on next page.)

*Primary Examiner*—Frederick E. Waddell
*Assistant Examiner*—Gregory Hook
*Attorney, Agent, or Firm*—Arnold, White & Durkee

[57] ABSTRACT

The present invention discloses unique methods employing mixtures of phospholipids and neutral lipids for surfactant replacement therapy in the treatment of the various forms of respiratory distress syndrome. These compositions are shown to greatly enhance the surfactant replacement efficiency of surface-active lipids. In this regard, experimental models have shown that both the surface-tension lowering effect and rate of phospholipid absorption to an air/liquid interface are accelerated by the addition of triglycerides and/or sterols to mixtures of saturated or unsaturated phospholipids. Such compositions are therefore theorized to give new and enhanced therapeutic value to the use of surface-active lipids for surfactant replacement therapy in a subject without risk of immunogenic response. The subject methods also comprise a simple, rapid and inexpensive means for the deposition of polar lipids to a variety of air/liquid interfaces.

30 Claims, 12 Drawing Sheets

U.S. PATENT DOCUMENTS

Hills et al. (1983), Gastric mucosal barrier: hydrophobic lining to the lumen of the stomach., Am. J. Physiol., 244:G561–G568.

Butler et al. (1983), Distribution of surfactants in the canine gastrointestinal tract and their ability to lubricate., Am. J. Physiol., 244:G645–G651.

Lichtenberger et al. (1983), Role of Surface-Active Phospholipids in Gastric Cytoprotection., Science, 219:1327.

Dial et al. (1984), A Role for Milk Phospholipids in Protection Against Gastric Acid., Gastroenterology, 87:379–385.

Lichtenberger et al. (1985), Effect of 16,16–Dimethyl Prostaglandin $E_2$ on the Surface Hydrophobicity of Asprinin-Treated Canine Gastric Mucosa., Gastroenterology, 88:308–314.

Namiot et al. (1987), Triacylglycerol and glycogen concentrations in the gastric and duodenal mucosa in patients with the differences in acid secretion., Chemical Abstracts, 106:48070, Abstract #48070g.

Barrow, R. E., and Hills, B. A. (1979), "Surface tension induced by dipalmitoyl lecithin in vitro under physiological conditions," J. Physiol., 297:217–227.

Hills, Brian A. (1982), "What forces keep the air spaces of the lungs dry?" Reprinted from Thorax, 37:713–717.

Clements, John A. et al. (1960), "Pulmonary surface tension and alveolar stability," J. Physiol., 217:414–450.

Barrow, R. E., and Hills, B. A. (1979), "A critical assessment of the Wilhelmy method in studying lung surfactants," J. Physiol., 295:217–227.

King, Richard J., and Clements, John A. (1972), "Surface active materials from dog lung. I. Method of Isolation," J. Physiol., 223(3):707–714.

Schoephoerster, Richard T. et al. (1985), "A survey of polar and non–polar lipids of mouse organs," Comp. Biochem. Physiol., 82B(2):229–232.

Shapiro, D. L., "Development of Surfactant Replacement Therapy" (Chapter 1), in Surfactant Replacement Therapy, Shapiro, D. L. and Notter, R. H., Eds., Alan R. Liss, Inc., New York (1989) 1–17.

Robertson, B., "Surfactant Deficiency and Lung Injury" (Chapter 6), in Surfactant Replacement Therapy, Shapiro, D. L. and Notter, R. H., Eds., Alan R. Liss, Inc., New York (1989) 127–144.

Enhorning G., "Animal Experiments Preceding the Clinical Use of Pulmonary Surfactants" (Chapter 8), in Surfactant Replacement Therapy, Shapiro, D. L. and Notter, R. H., Eds., Alan R. Liss, Inc., New York (1989) 163–177.

Phibbs et al. (1991), Initial Clinical Trial of EXOSURF, A Protein–Free Synthetic Surfactant, for the Prophylaxis and Early Treatment of Hyaline Membrane Disease., Pediatrics, 88(1)1–9.

Hoekstra et al. (1991), Improved Neonatal Survival Following Multiple Doses of Bovine Surfactant in Very Premature Neonates at Risk for Respiratory Distress Syndrome., Pediatrics, 88(1):10–18.

Liechty et al. (1991), Reduction of Neonatal Mortality after Multiple Doses of Bovine Surfactant in Low Birth Weight Neonates with Respiratory Distress Syndrome., Pediatrics, 88(1):19–28.

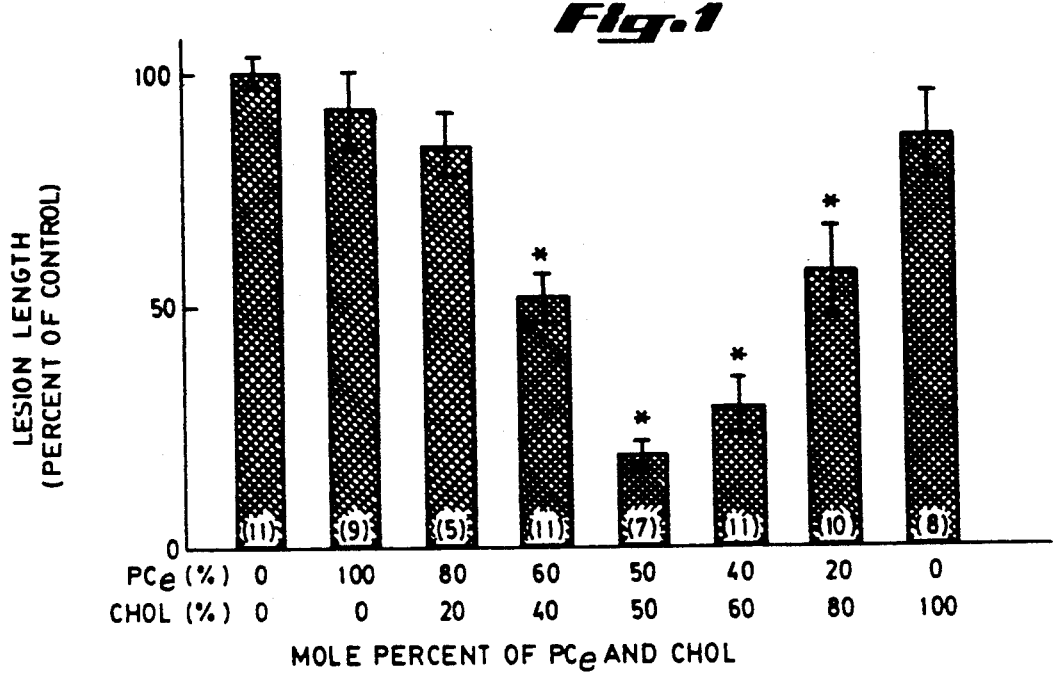
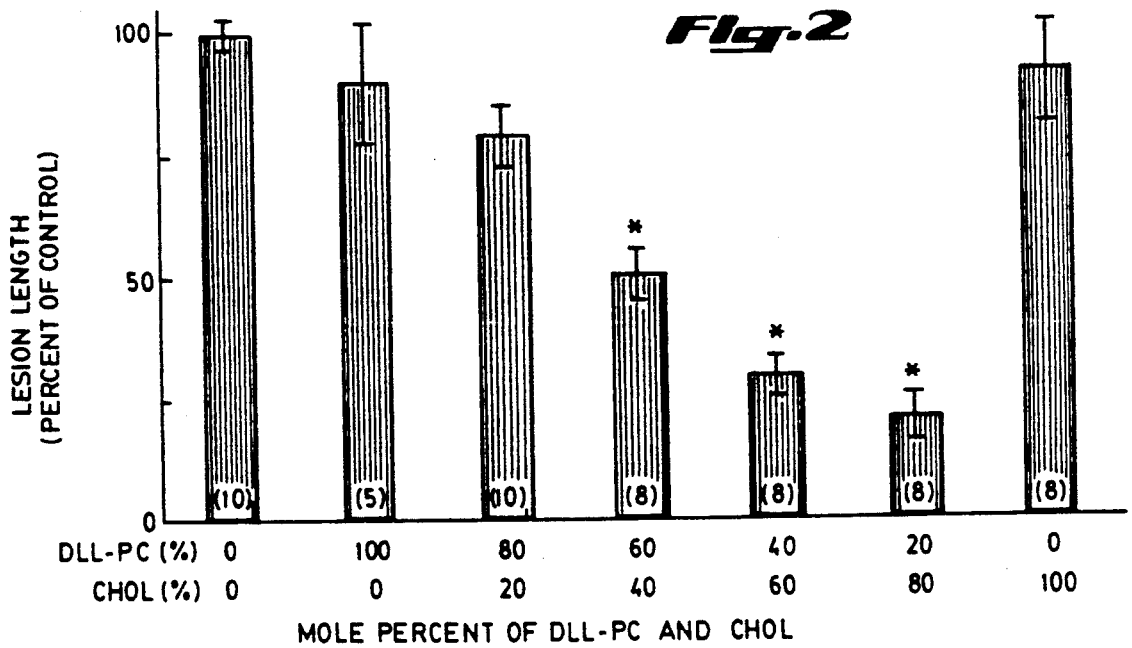

TIME AFTER ADMINISTRATION (hours)

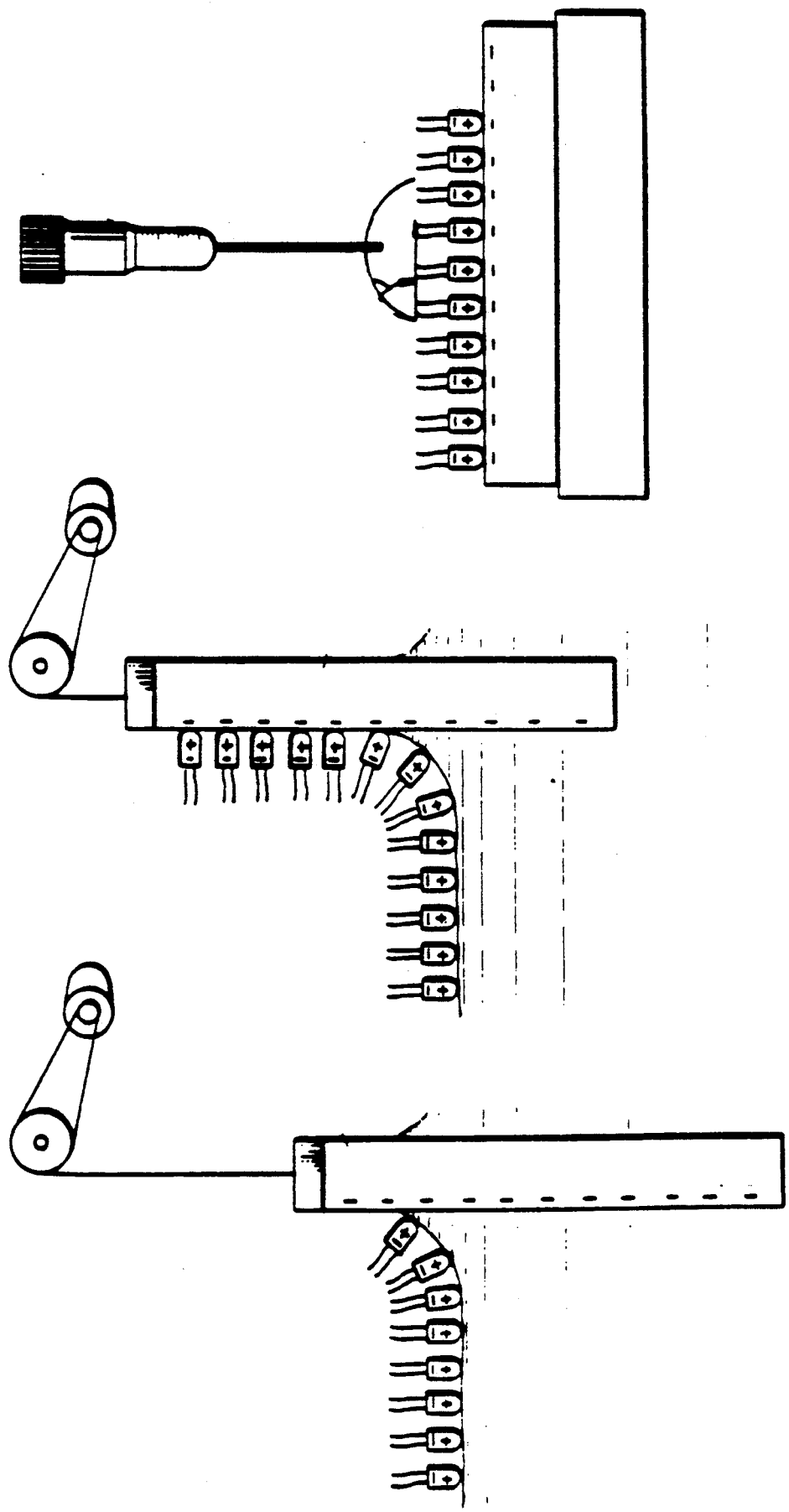

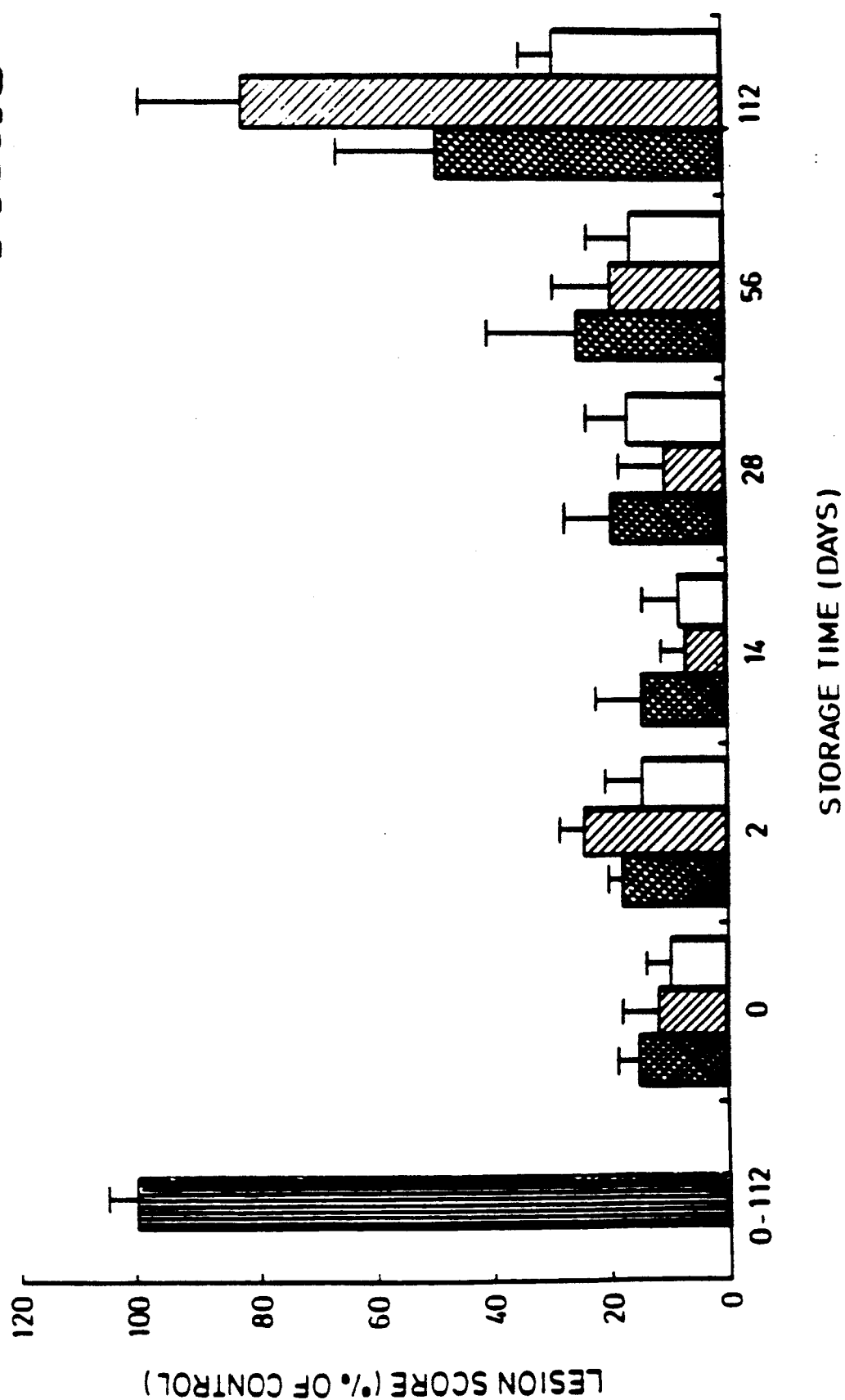

METHODS EMPLOYING UNIQUE MIXTURES OF POLAR AND NEUTRAL LIPIDS AND STEROL FOR LUNG SURFACTANT REPLACEMENT THERAPY

BACKGROUND OF THE INVENTION

The government may own certain rights in the present invention pursuant to NIH grant AM 33239 and DK 33239. Reference is hereby made to U.S. Ser. No. 015,394 filed Feb. 17, 1987 now U.S. Pat. No. 4,918,063.

The present application is a divisional application of pending U.S. Ser. No. 636,672, filed Feb. 4, 1991, now U.S. Pat. No. 5,134,129, priority is claimed. U.S. Ser. No. 636,672, now U.S. Pat. No. 5,134,129, is a divisional application of U.S. Ser. No. 323,671, filed Mar. 15, 1989, now U.S. Pat. No. 5,032,585, and is also asserted as a basis of priority for the present application. U.S. Pat. No. 5,032,585 is a continuation-in-part application of U.S. Ser. No. 015,394, filed Feb. 17, 1987, now U.S. Pat. No. 4,918,063 Reference is hereby made to U.S. Ser. No. 015,394, filed Feb. 17, 1987, now U.S. Pat. No. 4,918,063.

Priority to U.S. Pat. No. 4,918,063, is claimed in the present application, as a continuation chain of copendency has been maintained through the foregoing chain of applications to the filing date of the present application.

Field of the Invention

The present invention relates to pharmaceutical compositions and methods for protecting the luminal lining of the gastrointestinal tract from ulceration. In particular, the present invention relates to compositions which include unique mixtures of phospholipids, triglycerides and/or cholesterol which are useful for the treatment or prevention of ulceration of the lining of the gastrointestinal tract.

The present invention also relates to methods and compositions for surfactant replacement therapy and other conditions requiring rapid phospholipid adsorption to surfaces, such as Respiratory Distress Syndrome (RDS).

Description of the Related Art

Gastrointestinal ulcer disease, in particular, peptic ulcers, affect 5-15% of the United States population. Moreover, this disease is not restricted to the more industrialized Western culture—indeed, gastric ulceration is even a more serious problem in the Orient. One ulcer disease, particularly worrisome to pediatricians, occurs in premature infants. This condition, known as necrotizing enterocolitis, affects 10-15% of newborns having a birth weight of under 1.5 kg and results in severe ulceration of the small intestine, which frequently requires surgery. The etiology of this condition, like that of peptic ulcer disease, is not understood but it has been postulated that the primary defect lies in an abnormal mucosal defense mechanisms against luminal damaging agents.

Severe ulceration of the gastrointestinal mucosa can also spontaneously occur in the lower bowel (distal ileum and colon) in a spectrum of clinical disorders called inflammatory bowel disease (IFBD). The two major diseases in this classification are Ulcerative Colitis and Crohn's Disease which are associated with severe mucosal ulceration (frequently penetrating the wall of the bowel and forming strictures and fistulas), severe mucosal and submucosal inflammation and edema, and fibrosis. Clinically, patients with fulminant IFBM can be severely ill with massive diarrhea, blood loss, dehydration, weight loss and fever. The prognosis of the disease is not good and frequently requires resection of the diseased tissue. The etiology of IFBD is also poorly understood.

There are many drugs currently on the market to treat peptic ulcer disease. Most of these drugs are directed to neutralizing or inhibiting gastric acid secretion. Notable of the antiulcer compositions are anticholinergics and antihistamines both of which can result in a multitude of undesirable side effects in addition to blocking gastric acid secretion. This form of therapy is based on the tenet "no acid, no ulcer". Although it appears that peptic ulcers will not form in the complete absence of gastric acid, it is generally recognized that not all ulcer patients exhibit enhanced gastric acid output. In fact, gastric ulcer patients as a group have abnormally low gastric acidity. Thus, it has been suggested that gastric acidity may only be an aggravating factor and not a primary cause of gastrointestinal ulcerogenesis.

There is little consensus on the proper medical treatment of necrotizing enterocolitis. Frequently afflicted infants are managed by intravenous hyperalimentation and surgery when life-threatening strictures or perforations result. The medical treatment of inflammatory bowel disease in general is directed to controlling rather than curing the disease. Typical protocols employ steroids and the sulfa drug, Azulfidine (Salicylazosulfapyridine). Although these drugs reduce the mucosal inflammation, diarrhea and even blood loss in chronic inflammatory processes, they have little efficacy in treating the more fulminant forms of the disease. Furthermore, they cause a host of side effects of varying severity in the patients.

An alternative explanation of ulcer incipiency involves the belief that G.I. ulceration develops in individuals that have a defect in a putative "gastrointestinal mucosal barrier." This defect permits luminal damaging agents (acid, enzymes, bile salts, bacteria) to penetrate the surface lining and thereafter promote ulcerogenesis.

It is presently unclear how the normal gastrointestinal (G.I.) epithelium protects itself from these insults. Indeed, the answer to this fundamental question has long been sought, since it certainly remains a paradox why the stomach does not digest itself while it is constantly bathed in a extremely acidic and proteolytic environment. Conversely, the clinically important question remains as to how and why the element of protection is removed or circumvented in peptic ulcer disease, necrotizing enterocolitis and inflammatory bowel disease. A great deal of research has been performed to answer these important questions. Investigators have postulated that the mucosa is protected by a putative "gastrointestinal mucosal barrier" which prevents the back diffusion of hydrochloric acid and other potentially toxic agents from the lumen into the epithelium. Disruption of this mucosal barrier, results in the development of G.I. erosions. Although a wide variety of damaging agents such as aspirin, bile salts, hydrochloric acid and alcohol certainly will cause G.I. ulceration if present in high enough concentrations, it is generally believed that the primary cause of ulcer disease in a majority of patients is attributable to a natural defect in the "G.I. mucosal barrier."

Unfortunately, as noted above, most of the existing pharmacological approaches to the treatment of gastrointestinal disease are directed to treating either the gastric acid secretions, for example, through the use of anticholinergics, antihistaminics, and/or antacids, reducing mucosal and submucosal inflammation (steroids) or by physically treating the ulcer itself, for example, with a coating agent such as sucralfate. While the treatment of gastric acid secretion has served to provide some degree of symptomatic and pain relief and occasionally promote ulcer healing, their use is often complicated by undesirable side effects and/or promotion of an acid rebound effect. Sucralfate, on the other hand, is directed to treating the ulcerated tissue directly by forming a physical barrier to gastric contents, and thus does not serve an ulcer preventative function. Moreover, peptic ulcers readily recur at a high rate once patients are withdrawn from therapy with $H_2$ antagonists or sucralfate. Similarly the underlying defect in the mucosal barrier which increases a patients susceptibility to inflammatory bowel disease has yet to be identified and it is clear that our present forms of medical therapy for this condition merely treat the symptoms instead of the origin of the disease.

It has been observed by the present inventor that the mucosal surface of certain regions of the gastrointestinal tract have remarkable hydrophobic characteristic that make it non-wettable (i.e.—water repellant) to the luminal contents. It was of interest that the most hydrophobic gastrointestinal tissues (e.g., the stomach, esophagus and colon) are those regions most susceptible to mucosal ulceration or inflammation. Furthermore, it has been observed that experimental chemicals which induce gastric ulcerogenesis or colitis in laboratory animals result in a marked attenuation of the non-wettable property of the affected mucosal region.

Accordingly, the present invention derives in part from such observations by recognizing a need for a treatment method which is directed to restoring or maintaining the normal hydrophobic character of the luminal lining and thereby prevent or retard the deleterious effects of cytotoxic chemicals in the lumen (e.g., $H^+$, proteolytic enzymes, endotoxin) to the mucosal lining. Moreover, there is a need for essentially non-toxic agents which may be administered in a convenient dosage form, for example, in a liquid or suspension form, that is well tailored to treat the luminal lining quickly and effectively.

Respiratory Distress Syndrome (RDS) is a debilitating lung disease which is characterized by a decrease in the surface-active material at the air/liquid interface or the pulmonary alveolus. The descriptive term "RDS" has been applied to many acute diffuse infiltrative lung lesions of diverse etiologies when they are accompanied by arterial hypoxemia. Diseases classified generally as Respiratory Distress Syndrome (RDS) range from adult respiratory distress syndromes (ARDS) to a neonatal form, termed variously as idiopathic RDS or hyaline membrane disease. The term RDS is applied to the various forms because of several clinical and pathologic similarities between such acute illnesses in adult and neonatal forms.

Normal lung function depends on the presence of an alveolar lining layer with properties that permit alternate increases and decreases in surface tension, thus, allowing continuous and rapid exchange of $O_2$ and $CO_2$ throughout the respiratory cycle. To function properly in the exchange of gases and to maintain its structural integrity, the alveolar lining must retain both its elasticity and stability. The principal mechanism employed by the body to maintain these alveolar properties is through the production of surfactant, primarily by type II alveolar cells. Failure to produce a sufficient amount of surfactant results in both a marked decrease in alveolar elasticity (hence the name, hyaline membrane disease) and alveolar collapse before end-stage expiration resulting in a marked reduction in gas exchange for subsequent respiratory cycles. It is these conditions involving reductions in lung surfactant with which the present invention is also concerned.

Natural lung surfactant is a lipid composition which includes a complex mixture primarily containing phospholipids, certain neutral lipids and proteins, with lipids making up 80% of the composition. The lipid component is composed mainly of dipalmitoyl phosphatidylcholine (dispalmitoyl lecithin), phosphatidyl-glycerol, phosphatidylethanolamine, triglycerides cholesterol and cholesterol esters. The protein components of surfactant required for full surfactant properties include a family of apoproteins. The presence of a number of these apoproteins has been shown to enhance the rate of surface-film formation (see, e.g., Whitsett et al. (1986), *Pediatr. Res.*, 20:460; Avery et al. (1986), *New Engl. Jrnl. Med.*, 315:825).

The treatment of respiratory distress diseases has traditionally been limited to supportive care, including, for example, oxygen administration or even mechanical ventilation. Forced ventilation is not only an inadequate treatment in most severe cases of RDS and surfactant-deficiency RDS, it places mechanical stress on the lungs and diaphragm and can lead to severe alveolar trauma or even pneumothrax.

More recently, progress has been made in the treatment of neonatal and adult Respiratory Distress Syndrome (RDS) by surfactant replacement therapy. (See, e.g., Fujiwara, T., Pulmonary Surfactant (1984); Takahashi, et al. (1986), *Biochem. Biophys Res. Comm.*, 135:527–532; Metcafe, et al. (1980), *J. Appl. Physiol.* 49:34–40). These surfactant-replacement methods involve the intratracheal instillation of various surfactant mixtures in an attempt to replenish lung surfactant content exogenously. One such surfactant mixture includes dipalmitoyl phosphatidylcholine (DPPC). Corticosteroids have also found some utility in the treatment of RDS, particularly when administered to expectant mothers of premature infants (see, e.g., Ballard et al. (1980), *J. Pediatr.* 97:451; Papegeorgiou et al. (1981), *Pediatrics.* 67:416).

Although DPPC is one of the most prominent and surface active of the lipids in pulmonary surfactant, it has been learned that DPPC alone has only marginal therapeutic value. Corticosteroid therapy which has limited effectiveness is also undesirable under certain circumstances due to its multiple systemic actions, for example, as a direct treatment in premature infants or in patients sensitive to corticosteroids Although pulmonary installations of mixtures of surface active phospholipids and surfactant-specific apoproteins appear to be an attractive alternative in surfactant replacement therapy (See Hawgood, et al. (1986), *Biochem* 24:184–190) such a treatment will require significant additional development and expense to identify, purify, clone and/or synthesize the proteins in question before such a treatments therapeutic value may be assessed. Additionally, the possible disadvantage that the surfactant-associated proteins may be immunogenic exists. The use of crude and semipurified bovine pulmonary surfacts in surfactant replacement therapy also presents the disadvantage of being immunogenic, thus inducing an immune reaction in a patient who is already in a debilitated state suffering from RDS. (See Fumiwara, T. Pulmonary Surfactant (1984); Takahashi, et al. (1986) *Biochem. Biophys. Res. Comm.* 135:527–532).

Unfortunately, present and postulated RDS treatment protocols such as the foregoing fail to provide adequate treatment of all or most cases of RDS. Although purified DPPC has been shown to elicit important surfactant properties in the lungs such as to lower alveolar surface tension and to promote alveolar gas exchange and an increase in the $PO_2$ content of blood, these effects only occur after an extended amount of time (16–20 hours post-administration). The therapeutic effectiveness of DPPC treatment would therefore be greatly enhanced if a method of accelerating the rate at which DPPC molecules spread over an air/liquid interface while maximally lowering surface tension were developed which did not have the potential complications of systemic side affects or allergic reactions. Such would present an effective surfactant replacement treatment for RDS and other surfactant requiring conditions.

SUMMARY OF THE INVENTION

In its most general and overall scope, the present invention is directed to the realization that by treating the luminal surface of the gastrointestinal tract with an agent having the ability to increase or maintain its hydrophobic character, the luminal lining may thereby be protected from the deleterious effects of aqueous cytotoxic chemicals in lumen, for example, gastric acid and digestive enzyme secretions. The invention is directed in particular to unique mixtures of zwitterionic phospholipids together with neutral lipids, for example, sterols and/or triglycerides, which can provide the luminal lining with a very consistent, rapid acting and longlasting protection from chemical and idiopathic gastrointestinal ulcerogenesis. Thus, the term phospholipids, as referred to herein, relates generally to phospholipids which have a positively charged nitrogen at the site of application. For example, the amine may be either a quaternary amine or an amine that is ionized at the pH of the stomach.

Pharmaceutical compositions of the present invention, in one embodiment, include a saturated phospholipid having aliphatic substitutions ranging from 8 to 32 carbon atoms, together with a saturated triglyceride, having saturated aliphatic substitutions ranging from 4 to 32 carbon atoms, the phospholipid and triglyceride being disposed in a pharmaceutically acceptable diluent.

As used herein, a saturated phospholipid is defined as a phospholipid containing only saturated aliphatic substitutions of from 8 to 32 carbon atoms, and saturated triglyceride is defined as a triglyceride having saturated aliphatic substitutions of from 4 to 32 carbon atoms.

Although virtually any combination of a saturated phospholipid and saturated triglyceride will provide the benefits of the present invention, in a referred embodiment the saturated phospholipid is dipalmitoyl-phosphatidylcholine (DPPC), dimyristoyl phosphatidylcholine, distearoyl phosphatidylcholine, and the saturated triglyceride is tripalmitin (TP), trimyristin, and/or tristearin.

Although it has previously been found that saturated phospholipids have some degree of antiulcer activity in and of themselves, the present invention embodies the discovery that the addition of a triglyceride (preferably saturated) to the saturated phospholipid-containing composition will enhance the antiulcer effect of the saturated phospholipid to a surprising extent. For example, when the saturated phospholipid dipalmitoyl phosphatidylcholine (DPPC) is intragastrically administered to rats at a low threshold concentration of 1 mg/ml, 2 hrs prior to being challenged with strong acid, a marginal 5–10% reduction in lesion score is recorded. In contrast, addition of the saturated triglyceride tripalmitin (TP) to the DPPC suspension induced a dramatic dose-dependent increase in protection against acid-included gastric ulcerogenesis with <90% reduction in lesion score being recorded when TP was added at concentrations of 4 mg/ml or greater. Furthermore, the protection provided by this mixture was observed to be long-lasting, with lesion score reduced by 75% when the lipids were administered 6 hrs prior to the acid challenge.

Interestingly, compositions which include only a saturated phospholipid together with an unsaturated triglyceride have a lessened antiulcer activity in the experimental systems employed by the present inventor. Moreover, saturated phospholipid-containing compositions are found to lose their activity upon the addition of stoichiometric amounts of cholesterol, or other sterols, to the mixture. Although it is unclear why this is the case, it is hypothesized that the addition of cholesterol, or other sterols, to saturated phospholipid-containing compositions apparently serves to disrupt the association of phospholipid structures and thereby prevents their interaction with the luminal lining to form a uniform hydrophobic lining.

In one embodiment of the anti-ulcerogenic invention, the saturated phospholipid and saturated triglyceride ar included i weight ratios ranging from 1:1 to 1:10, and more preferably in weight ratios ranging from 1:2 to 1:5. In fact, a weight ratio of 1;4 has been found to provide the most superior antiulcer activity of all of the presently disclosed antiulcer compositions.

In further anti-ulcerogenic embodiments, pharmaceutical compositions are provided which comprise an ulcer protective amount of the combination of an unsaturated phospholipid, defined as a phospholipid having at least one unsaturated aliphatic substitutions ranging from 8 to 32 carbon atoms, together with a sterol having an aliphatic substitution of from 1 to 10 carbon atoms at the number 17 carbon, both together in a pharmaceutically acceptable diluent.

Although cholesterol is the preferred sterol, other sterols such a desmosterol, beta-sitosterol, campesterol or estradiol will function equally well. However, in that it is generally desirable to keep the potential toxicity of the present compositions at a minimum, it is suggested that only nonbiologically-active sterols be included. Therefore, for example, one would not typically desire to include a sterol having hormonal activity such as an estrogen, androgen, corticosteriod, progestigen, or ability, low cost and lack of potential toxicity, cholesterol id desirably employed in the formulation of unsaturated phospholipid-containing compositions. Further, sitosterol, a plant sterol with negligible athrosclerotic potential can be substituted for cholesterol without diminishing the gastric protective activity of the lipid mixture.

In a preferred embodiment, the unsaturated phospholipid and sterol-containing compositions are formulated to include the unsaturated phospholipid and sterol in mole percent ratios ranging from about 4 to about 0.25, or more preferably, in mole percent ratios ranging from about 1.5 to about 0.25, respectively.

In certain preferred embodiments, the unsaturated phospholipid and sterol-containing compositions are formulated to include egg phosphatidylcholine, or the poly-unsaturated dilinoleoyl-phosphatidylcholine. However, virtually any lipid as defined herein will provide benefits in accordance with the invention.

It has further been determined that the antiulcer activity of unsaturated phospholipid and sterol-containing compositions is greatly improved upon the addition of a triglyceride to the formulation. The triglyceride in such compositions may be either saturated or unsaturated. However, it has been found that there is some degree of preference in terms of which saturated or unsaturated triglyceride is employed with which unsaturated phospholipid. For example, it is preferred to employ dilinoleoyl phosphatidycholine (DLL-PC) with the saturated triglyceride tripalmitin. However, where the selected unsaturated phospholipid is egg phosphatidylcholine, the preferred triglyceride is the unsaturated triglyceride triolein.

It should be noted that the protective activity of the lipid mixtures of the present invention does not depend upon the ester bonding between the fatty acid side chain and the constituent phospholipid and/or triglyceride. Full activity is retained when the ester bonding is substituted with an ether bonded fatty acid side chain. As shown at FIG. 11, the protective effect of DPPC-TP against acid-induced gastric lesions remained the same when either one or both of the ester lipids were substituted by inert ether analogues.

The mixtures of polar and non-polar lipids, whether based on saturated or unsaturated phospholipids, are typically formulated into liposomal, mixed micellar, colloidal or microemulsion suspensions using an aqueous medium or diluent to provide a composition having a concentration ranging from about 0.5 to about 10 mg/ml of suspension, depending upon the intended application and ulcer-protective strength of the combination employed. For example, for the treatment of peptic ulcer disease by oral administration to the stomach, a dose range of from 1 to about 4 mg/ml is generally preferred. However, for application to be the lower bowel, higher concentrations may be indicated, particularly for more severe luminal erosions such as in ulcerative colitis.

Although the particular aqueous diluent is not particularly crucial, Applicant has found that isotonic saline provides a consistently stable and efficacious formulation. However, it is believed that lipid deposition and adsorption to the mucosal surface may be accelerated by the presence of polyvalent cations in the diluent solution.

In formulating the phospholipid mixtures, the desired amount of the selected lipids are simply placed into a suitable container and an appropriate amount of isotonic saline, or other aqueous medium, added. The entire mixture is then vortexed, sonicated or otherwise vigorously admixed for several minutes to suspend the lipids. In some cases the temperature may be raised above the transition temperature for a phospholipid to promote the formation of a liposomal, mixed micellar, colloidal or microemulsion suspension. It has ben found that sonication is preferred for unsaturated phospholipid/triglyceride compositions as well as for other lipid compositions which include a saturated triglyceride. For other unsaturated phospholipid-containing compositions, vortexing is generally preferred.

Compositions formulated in this manner are generally stable for at least one week, and typically longer, either at 4° C. or room temperature However, some degree of settling of the lipids may occur upon storage of the composition for extended periods. Upon settling, the compositions may be readily regenerated by simply shaking or vortexing it to resuspend the lipids. There is generally no requirement that lipid aggregates be dispersed in that generally such aggregates have been found to exhibit the same or greater activity as totally dispersed suspensions.

In general, it has been determined that the addition of a polyvalent cation, for example (many of which are classified as heavy metals), to the formulation of any of the foregoing compositions will improve their antiulcer activity. It is hypothesized that the polyvalent ions interact with the negatively charged phosphate groups of the phospholipid in a manner to facilitate its adsorption to the luminal lining as a compact monolayer and thereby increase its efficacy in maintaining luminal hydrophobicity. It is postulated that virtually any polyvalent cation, and in particular, heavy metal ion, will function in this regard, and should typically be included in a molar ratio of between about 0.5 and 20 moles of phospholipid to moles of metal ion. Due to their potential toxicity, certain heavy metals should not be employed, for example, mercury, which has a very high nephrotoxicity. However, polyvalent cations such as copper, zinc, gold bismuth, aluminum or calcium are generally well tolerated at effective concentrations, and thus may be included to improve the efficacy of the phospholipid compositions. The polyvalent cations are typically added in the ionic state to the aqueous medium used to suspend the lipid mixtures.

The invention further embodies the realization that the addition of both lipid and water soluble vitamins (vitamins A, E and C) and other chemical anti-oxidants with the capability of scavenging free radicals can further enhance and prolong the anti-ulcer efficacy of these lipid mixtures. This is likely attributable to their ability to prevent the oxidative destruction of unsaturated phospholipids.

Accordingly, the present invention is directed in its most general scope to a method of protecting the luminal lining of the gastrointestinal tract of a subject against ulceration, the method including administering an effective amount of one of the foregoing compositions to the lining. Protection against ulceration is thus provided to the luminal lining by administering to it an amount of one of the foregoing compositions that is effective to maintain the hydrophobicity thereof.

The compositions of the present invention may be employed together with a non-steroidal antipyretic or anti-inflammatory agent, such as aspiring or the like, as a means of preventing or reducing other ulcerogenic side effects. The non-steroidal agents may be formulated into the compositions by including them into the aqueous diluent, by adding them to the compositions post-formulation, or by simply co-administering them together with the anti-ulcer composition. Where the lipids employed tend to form liposomes, for example, in the case of unsaturated phospholipid/cholesterol compositions, it may be particularly desirable to include the non-steroidal agent into the mixture prior to vortexing or sonication in that this will allow at least a proportion of the agent to be liposomally encapsulated; thereby improving the protective action of the lipid mixture. However, an adequate protective effect can be obtained by simple co-administration. Thus, such compositions, however formulated, will function to prevent the ulcerogenic action of such ulcerogenic agents and, in this embodiment, function to simultaneously provide the subject receiving such an agent with a suitable relief from pain, fever, bleeding, diarrhea and/or inflammation.

The present invention is further directed to the realization that by treating a surface with the above described compositions, the rate of phospholipid surface absorption at an air liquid interface would be greatly increased. Also, such would accelerate the rates at which the phospholipids induce both a surface-tension lowering, and surface hydrophobicity enhancing effect in both inert and biological systems. Thus, the invention has the ability to act as an improved form of surfactant replacement therapy for the treatment of various forms of respiratory distress syndrom (RDS), as well as numerous other medical and industrial uses. For example, a particular industrial use of the subject invention is the surfactant catalysis of oil recovery from oil spills in the open sea. More generally, the subject suspensions may be used in any circumstance where the rapid deposition of polar lipids to an air/liquid interface is required.

The subject invention also has significant application in the field of medicine as a rapid surfactant-replacement preparation. Compositions which include only the surface active lipid dipalmatoyl phosphatidylcholine have a lessened surfactant-replacement activity and surface tension lowering effect due to its slow rate of surface adsorption in the experimental systems employed by the present inventor. This lessened surfactant-replacement activity has also been observed in the form of nominal therapeutic value exhibited from clinical use of such compositions in the treatment of Respiratory Distress Syndrome by other investigators. (See Fujiwara, et al. (1984) *Pulmonary* surfactant, pp. 479-504); Meban, et al., *Pediatr. Res.* 1029-1031 (1981)).

The invention is thus directed in particular to unique mixtures of phospholipids together with neutral lipids, for example, sterols and/or triglycerides, which can rapidly replace or create a surfactant-like covering, and may in one application promote rapid phospholipid absorption to biological surfaces, notably the air/liquid interface of the pulmonary alveolus.

The particular pharmaceutical compositions for surfactant replacement include the saturated and unsaturated phospholipids (together with cholesterol) as previously described herein. Similarly, the saturated and unsaturated triglycerides of these compositions are the same as those described for the anti-ulcer compositions.

Although it has previously been found that saturated phospholipids have surface-tension and hydrophobic inducing activity in and of themselves, the present invention embodies the discovery that the additional of a triglyceride (preferably saturated) to a saturated phospholipids-containing composition will enhance the surface tension lowering effect, and also the rate of said effect, of the saturated phospholipid to a surprising extent. Also, contact angle analysis reveals that such an addition to a phospholipid mixture will increase the hydrophobicity of the treated surface and rate at which the surface hydrophobicity reaches its maximal value. For example, when the adsorption kinetics of the saturated phospholipid, dipalmitoyl phosphatidylcholine (DPPC), was studied as assessed by surface tension and contact angle analysis, it was observed that addition of the saturated triglyceride, tripalmitin, would reduce surface tension 5-8 dynes/cm lower than DPPC alone. This DPPC-TP effect was elicited within 5 minutes of application, in contrast to the 24 hours required for DPPC alone to make a much less dramatic reduction in surface tension. In agreement with these findings, contact angle analysis of slides prepared in conjunction with these experiments indicated maximal hydrophobic properties of 35°-37° were attained at 16-24 hours after DPPC alone. In contrast, a comparable or greater lipid-induced rise in contact angle was accomplished in less than 10 minutes after DPPC-TP treatment, with a maximal reading of 47°-49° occurring at or before 1 hour post-treatment. A higher contact angle reading, as will be recalled, is correlated to higher hydrophobicity of the surface.

Furthermore, it has been found that the ability of a triglyceride, such as tripalmitin (TP), to enhance the above surface properties is also dependent upon the molecular proportion of neutral to polar lipids in the composition. For example, the inclusion of DPPC:TP at a 2:1 wt.:wt. ratio (20 micrograms total lipid weight) resulted in surface tension readings of 60 dynes/cm 10 min after application to the bath. In contrast, DPPC:TP ratio of 1:2 and 1:3 wt.:wt. ratio (20 micrograms total lipid weight) resulted in surface tension readings of about 38 dynes/cm 10 min post-administration. These results are in agreement with contact angle analysis of a glass slide pulled through the bath 10 min after lipids were administered, which gave a contact angle of 20° for DPPC:TP at a 2:1 wt.:wt ratio, but a 50° contact angle for DPPC:TP at a 1:2 wt.:wt. ratio.

In one embodiment of the surfactant replacement composition, the saturated phospholipid and saturated triglyceride are included in weight ratios ranging from 1:1 to 1:5, and more preferably in weight ratios of from 1:2 to 1:4. In fact, a weight ratio of 1:3 has been found to provide the most superior surfactant activity of all of the presently disclosed surfactant compositions.

In further surfactant-replacement embodiments, pharmaceutical compositions are provided which comprise a surfactant-enhancing amount of the combination of an unsaturated phospholipid, as previously defined, together with a sterol, and/or triglyceride as previously defined, together in a pharmaceutically acceptable diluent.

Although cholesterol is the preferred sterol, other sterols such as demosterol, B-sitosterol, compesterol or estradiol will function equally well. As before, however, it is suggested that only non-biologically-active sterols be included. Due to its ready availability, low cost and lack of potential toxicity, cholesterol or the plant sterols sitosterol and/or campesterol are desirably employed in the formulation of unsaturated phospholipid-containing compositions.

In a preferred embodiment, the unsaturated phospholipid and sterol-containing compositions are formulated to include the unsaturated phospholipid and sterol in mole percent ratios ranging from about 4 to 0.25, or more preferably, in mole ratios ranging from about 1.5 to about 0.25, respectively.

As previously stated, the unsaturated phospholipid and sterol-containing compositions in certain preferred embodiments are formulated to include egg phosphatidylcholine, or the polyunsaturated dilinoleoyl phosphatidylcholine.

It has further been determined that the surfactant activity of unsaturated phospholipid and sterol-containing compositions is greatly improved upon the addition of a triglyceride to the formulation. (See FIG. 15). Although either saturated or unsaturated triglycerides may be used, some preference exists depending upon which unsaturated phospholipid is used. For example, it is preferred to employ the unsaturated triglyceride, triolein (TO) with the unsaturated triglyceride egg phosphatidylcholine. In one preferred embodiment, the weight ratio of phospholipid and sterol to the unsaturated triglyceride is 0.67:0.33:4.00. The phospholipid and sterol are preferably contained in equimolar concentrations. For example, a mixture of the above described preferred embodiment may contain about 0.67 mg. egg phosphatidylcholine, about 0.33 mg cholesterol and about 4 mg triolein.

The surfactant activity of the lipid mixtures of the present invention does not depend upon the ester bonding between the fatty acid side chain and the constituent phospholipid and/or triglyceride. As its true for all of the embodiments, full activity is retained when the ester bonding is substituted wit an ether bonded fatty acid side chain. (See FIG. 11).

All of the surfactant active compositions are formulated in the identical manner as described previously for the anti-ulcer formulations. (Specification, pg. 14, 15). Although the particular aqueous diluent employed is not imperative, isotonic saline is preferred. Additionally, it is contemplated that the addition of a polyvalent cation, for example, a heavy metal ion, to the formulation will enhance surfactant activity. The relative preferred molar concentrations are the same as those outlined for the anti-ulcer formulations. Potentially toxic metal ions should, again, be avoided.

Certain vitamins (vitamins A, E and C) and other chemical anti-oxidants are also to be included in the described surfactant compositions.

Accordingly, the present invention is directed to a method of preventing and treating respiratory distress syndrome, the method including administering an effective amount of one of the foregoing compositions to the pulmonary alveolus of the subject. Administration is preferably endotracheal, followed by 100% oxygen blown into the lungs with an anaesthetic bag. The subject is then to be ventilated with a respirator.

The surfactant compositions are thus capable of replenishing surfactant deficient biological surfaces, especially that of the pulmonary alveolar lining, through forming a cover over the alveolar lining layer. The alveolar lining layer (ALL) has been described as an acellular film that forms a continuous lining over the alveolar epithelial cells and spans the pores of Kohn. (E. Scorpelli and A. Mautone (1984) *Pulmonary Surfactant*. pp. 119-121). thus, the phospholipid covering is adjacent to, but not part of the cell itself.

Currently proposed phospholipid compositions typically consist of a preponderance of phospholipids and relatively low concentrations of neutral lipids. Applicant's compositions have a significantly greater concentration of neutral lipids (greater than 50%) to phospholipids (less than 50%). The neutral lipids are hypothesized to impart a greater buoyant density to a phospholipid molecule, thus enhancing the rate at which the phospholipid is moved toward an air/liquid interface and adsorbed. It is hypothesized that this novel combination and buoyant density effect are the reasons these compositions have such a surprisingly enhanced surfactant potentiating activity Moreover, Applicant's compositions may take on a variety of physical forms, including microemulsions. In contrast, other phospholipid compositions are primarily in liposomal form. Applicant theorizes that this difference too may contribute to the unexplained enhanced rate at which Applicant's compositions are able to elicit surface property changes in vitro. However, the scope of the present invention is not to be limited to the particular form of the composition.

BRIEF DESCRIPTION OF THE DRAWINGS

FIG. 1. A graphical illustration of the ulcer protective activity upon acid challenge of the combination of Egg phosphatidylcholine ($PC_e$) together with varying mole % amounts of cholesterol. The asterisks represent cholesterol embodiments showing the most clinically significant activity. Although neither $PC_3$ nor Chol protected against acid-induced gastric lesions on their own, unique mixtures of the polar and non-polar lipids have a clear protective action with a maximal 85% reduction in lesion score being produced by a mixture of $PC_e$+50 M% Chol. In this, and the subsequent experiments disclosed in the following figures (unless indicated otherwise), animals were intragastrically treated with 1 ml of the lipid test solution (total lipid conc=3 mg/ml), 2 hrs before being intragastrically challenged with 1 ml of 1N HCl. The rats were sacrificed 1 hr later at which time lesion score was analyzed under coded conditions.

FIG. 2. A graphical illustration of the ulcer protective activity, upon acid challenge, of the combination of dilinoleoyl phosphatidyl choline (DLL-PC) together with varying mole % amounts of cholesterol. As with FIG. 1, the asterisks are representative of preferred mole % rations. As with the FIG. 1 experiment, although neither DLL-PC nor Chol protected rats against acid-induced gastric lesions on their own, unique mixtures of the two lipids produced profound protection with a maximal (85% protection) effect being observed with a mixture of DLL-PC+80 M% Chol.

FIG. 14a-c. Schematic representation of the method employed in transferring the phospholipid monolayer at the air/liquid interface of the saline bath to a negatively charged glass slide. This transfer process increases the hydrophobicity of the glass slide as determined by contact angle analysis.

FIG. 19. The protective efficacy of lipid mixtures, stored over a period to time in amber bottles at 4° C. against 0.75 N, HCl challenge in adult rats.

DETAILED DESCRIPTION OF THE PREFERRED EMBODIMENTS

I. Introduction

Figure 3:
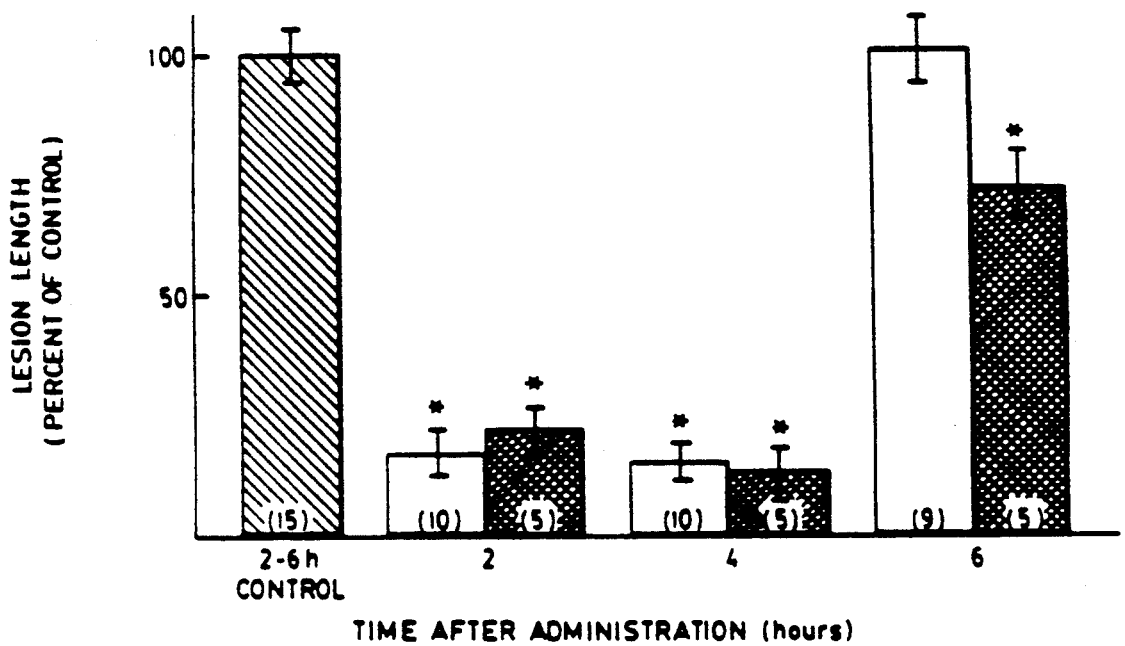
FIG. 3. Time-dependance of the protective effect of mixtures of unsaturated phospholipids (Egg-phosphatidylcholine, $PC_e$; and dilinoleoyl-phosphatidylcholine, DLL-PC) together with cholesterol (50 and 80 M%) against acid-induced gastric lesions. This graph illustrates the protective action of the mixtures of unsaturated phospholipid and cholesterol against acid-induced lesions was long-lasting and dissipated between 4-6 hrs post-injection. In this experiment the lipid mixture was intragastrically administered 2, 4 and 5 hrs prior to the acid-challenge. As before, the rats were sacrificed 1 hr after acid-challenge.

Recent studies by the present Applicant have indicated that many of the phospholipids found in a pulmonary fluid are also found along the length of the gastrointestinal tract, from the esophagus to the colon. These phospholipids appear to be concentrated on the mucosal surface which separates the digestive and absorptive epithelium from the luminal contents. The functional importance of phospholipids has been studied in greatest detail in the lung. It is now well recognized that pulmonary surfactants, which are high in phospholipids, play a vital role in minimizing the surface forces at the level of the alveoli, allowing the alveoli to remain open throughout the respiratory cycle.

There is a certain amount of evidence that the surface properties of surfactants also play a role in reducing the movements of extracellular fluids from the blood into the extracellular space. Perhaps related to this property, Applicant has recently found that surfactants, not unlike commercially available water repellants used to treat material surfaces, will make biological tissues non-wettable. This action provides the tissue with hydrophobic lining that will resist the penetration of water molecules across its surface.

In early experiments it was found that certain natural and synthetic phospholipids could both maintain the hydrophobic character of the luminal lining and retard the untoward effects of ulcerogenic compounds to a certain degree (see, for example, Lichtenberger et al. (1983), *Science*, 219:1327; Butler et al. (1983) *Am. J. Physiol.*, 244:G645; Hills et al. (1983), *Am. J. Physiol.*, 244:G562; and Dial et al. (1984), *Gastroenterology.* 87:379). However, the protective efficacy of these phospholipid suspensions varied widely between experiments, and when present was quite transient.

Upon further experimentation it has been found that mixtures of phospholipids together with neutral lipids, for example, sterols and/or triglycerides, can provide the luminal lining with rapid-acting, long-lasting and very consistent protection from chemical and idopathic gastrointestinal ulcerogenesis. For example, experimental findings, disclosed in detail below, demonstrate that mixtures of unsaturated phospholipids and cholesterol in various proportions can provide a marked protection from acid-induced ulcerogenesis. This protection if found to be surprisingly superior to the protection provided by unsaturated phospholipids alone which have either little or no protective action on their own. Moreover, this protective effect is even further enhanced upon the addition of a triglyceride, either saturated, unsaturated, to the mixture. Compositions formulated to include a saturated phospholipid together with a saturated triglyceride are found to provide the most effective protection.

Curiously, though, a much smaller enhancement in protective activity is obtained with compositions formulated to include a saturated phospholipid together with an unsaturated triglyceride. Moreover, the activity of saturated phospholipids standing alone is totally abolished by the addition of a sterol in stoichiometric amounts to the mixture. In contrast, unsaturated phospholipids, standing alone, appear to provide little or no protective effect and require the addition of a sterol such as cholesterol. The reason for this molecular specificity between polar and non-polar lipids is not known but may, in part, be attributable to the fact that saturated phospholipids and saturated triglycerides pack tightly with one another forming a compact and stable hydrophobic layer. Furthermore this level of organization is disrupted by the addition of cholesterol or unsaturated triglycerides to the mixture. In contrast by virtue of their non-linear fatty acid side chains unsaturated phospholipids do not pack tightly with one another and the addition of cholesterol and triglycerides to the mixture promote molecular contraction and stability of the hydrophobic layer. We also have evidence that the movement of phospholipids to an air/water interface is greatly accelerated (50-30 fold) by the addition of specific triglycerides to the mixture.

The lipids which are the subject of this invention are naturally occurring substances extractable from plant and animal sources or can be synthesized by various known processes. Furthermore, most of the lipids are commercially available, as they are starting materials for the wide class of soaps, pharmaceutical preparations, and biochemical research materials.

For oral administration, the compounds can be administered in substantially pure, undiluted form; as a supplement to infant formula or in various pharmaceutical dosage forms such as capsules, liposome carriers, microemulsions, aerosol sprays, dispersions, aqueous suspensions, solution, or the like. In that oral administration is typically the indicated route for treatment of gastric ulcer disease, a preferred composition for such application is a colloidal, microemulsion, mixed micellar or liposomal suspension of the phospholipid and associated neutral lipid. Moreover, suspensions may be indicated for other routes as well, such as administration to the lower bowel by means of an enema, or for direct infusion to the bowel.

While wishing not to be limited to the following theory, Applicant's invention is based on the principle that the zwitterionic phospholipids which carry a positive terminal charge, will be attracted to the negatively charged surface membrane or mucosa lining of the G.I. tract. These molecules will in turn orient in such a way so that their long hydrocarbon chains are extending outwards into the lumen. This results in the formation of a uniform hydrophobic layer over the tissue, which cannot be penetrated by hydrophobic damaging agents. This prevents water soluble damaging agents (e.g., acid, microbial toxins, proteolytic enzymes) from coming in contact with the tissue, and protects the tissue from injury. When the hydrocarbon side chains are not straight, for example, due to the presence of cis unsaturated bonds, cholesterol or other chemically related sterols are believed to be required to promote molecular packing. In turn, the sterol molecule is believed to enhance the hydrophobicity of the hydrocarbon layer. The thickness and stability of this layer may be increased substantially by the addition of triglycerides to the mixture, which may coat the luminal aspects of the adsorbed phospholipid (and cholesterol) layer by undergoing hydrophobic bonding with the extending fatty acid side-chains.

As indicated above it is believed that the addition of neutral lipids, in the form of glycerides or sterols, to the phospholipid compositions appear to stabilize this interaction with the luminal lining and accelerate its surface deposition. This stabilization effect is most readily demonstrated by, for example, both the increase in duration of activity, and in the increase on both efficacy and potency of the antiulcer protection of the neutral lipid containing compositions over compositions which include only phospholipids. Again, the mechanism is unclear. Another explanation may lie int he finding that the addition of neutral lipids to the suspension of charged lipids (i.e.—zwitterionic phospholipids) appears to accelerate the deposition of precipitation of the lipid complex from the suspension of the surface in question. Thus, phospholipid suspensions containing neutral lipids may coat biological surfaces at a faster rate and to a greater extent than the phospholipids standing alone.

In the practice of this invention, Applicant has found that gastric mucosa pretreated with either synthetic or natural phospholipids becomes virtually chemically resistant to luminal acid. This property was most dramatically demonstrated in vivo, where it was observed that rats pretreated with phospholipid resisted severe gastric mucosal damage after direct challenge to a strong solution of hydrochloric acid. In contrast, saline treated rats suffered severe gastric erosion and hemmorrhage. In vitro transport studies demonstrated that acid ($H^+$) diffuses much more slowly across gastric mucosa exposed to luminal phospholipid surfactants than across untreated tissue. Similarly, specific mixtures of phospholipids (and/or sterols) and triglycerides protected rats from a number of other ulcerogenic conditions including stress ulceration, intragastric ethanol, bile acid and aspirin.

The vital role of pulmonary surfactants in minimizing the surface forces of the lung alveoli has long been recognized. However, surfactant replacement therapy utilizing the most surface active of these phospholipids alone has been shown to be of marginal therapeutic value. (See Ikegami, et al. (1977) *Pediat. Res.* 11:178-182; Fujiwara, et al. (1979) *IRCS Med Sci.* 7:311; Meban, C., (1981) *Pediat. Res.* 15:1029-1031). The most prominent and surface-active of these lipids, diapalmitoyl phosphatidylcholine (DPPC), administered by intratracheal instillation, is a specific surface-active lipid which is used in surfactant replacement therapy. Treatment with DPPC alone is unlikely to be of great therapeutic value used alone owing to its slow rate of adsorption at air-fluid interfaces and its marginal ability to reduce surface-tension several hours after administration (See id.).

The adsorption of surface-active materials is a complex phenomenon. A number of factors affect the rate of adsorption. For example, which molecules or two or more surface-active agents accumulate at the free surface of a solution has been shown to depend principally on the concentration of the agents, the nature of the amphiphilic groups in the agents and the separation of these groups (chain length), the nature of the molecular interaction between the agents, the diffusion coefficient of the solution, and the temperature. (See J. Davies and K. E. Rideal, *Inter facial Phenomena* (1963); J. L. Moilliet, B. Collie, and W. Black, *Surface Activity* (1961)).

Early studies on the kinetics of surface adsorption of lipids, in particular dipalmitoyl phosphatidylcholine, with certain neutral phospholipids and crude lipid extracts of bovine pulmonary lavage fluid, suggest that the rate of DPPC adsorption could be enhanced by the addition of other lipids or proteins. For example, the addition of either dipalmitoyl phosphatidylglycerol, phosphatidylinositol, serum high-density lipoprotein or surfactant apoprotein to dipalmitoyl phosphatidylcholine (DPPC) was shown to markedly reduce DPPC adsorption time. (See Meban, C. (1981) *Pediatr. Res.* 150:1029-1031). For example, adsorption time was reduced from $91.8 \pm 8.3$ minutes for DPPC alone to $1.1 \pm 0.2$ minutes (+dipalmitoyl phosphatidylglycerol), $2.8 \pm 0.4$ minutes (+phosphatidylinositol), $1.0 \pm 0.2$ minutes (+serum high-density lipoprotein) and $0.9 \pm 0.1$ minutes (+surfactant apoprotein). However, the maximal level of surface tension reduction was not affected by the addition of those same substances to DPPC ($35.8 \pm 2.7$, $34.9 \pm 2.4$, $35.8 \pm 2.6$ and $34.5 \pm 2.7$ dynes cm respectively, maximum surface pressure of absorbed film (mN/M) compared to $35.6 \pm 2.6$ for DPPC alone).

Upon further experimentation, it has been found that mixtures of phospholipids together with neutral lipids, for example, sterols and/or triglycerides, can theoretically provide the alveolar lining with an increased surface hydrophobicity and a dramatically accelerated rate of surface-active lipid adsorption. Surface tension is also maximally reduced by these mixtures. For example, experimental findings, disclosed in detail below, demonstrate that mixtures of saturated phospholipids and triglycerides in various proportions can provide an enhanced rate of lowering surface tension and increase hydrophobicity through increased surface adsorption of lipids. These rates of adsorption and lowered surface tension have been found to be surprisingly superior to those provided by a surface-active lipid alone, which have either little or no therapeutic value on their own. Moreover, these surface tension lowering effects and rates of adsorption of unsaturated phospholipids (PCe) are enhanced upon the addition of a sterol, such as cholesterol, to the mixture. Compositions formulated to include a particular unsaturated phospholipid together with a triglyceride (i.e., TO) and sterol are found to provide the most rapid adsorption kinetics.

For intratracheal administration, the composition is to be administered as a suspension in saline or other physiologically acceptable diluent or a s a lyophilized powder. In that intratracheal administration is typically the indicated route for treatment of respiratory distress syndrome, a preferred composition for such application is a colloidal suspension or microemulsion of the particular saturated or unsaturated phospholipid and associated neutral lipid. The infusion of such a liquid or powder instillate into the endotracheal tube of a subject is followed by the blowing of 100% oxygen into the lungs with an anesthetic bag. Additionally, the compositions may be used in the treatment of other diseases where biological surfaces suffer from surfactant depletion, for example, in the treatment of otitis and ocular disease. A suspension of the compounds in any acceptable diluent may also be used to create the subject composition for various industrial uses, and therefore need not be in a physiological diluent. For example, water may be used as an acceptable diluent in the preparation of the subject compositions for use as an industrial surfactant in catalyzation of oil recovery from spills in the open sea. These compositions may be used anywhere the rapid deposition of polar lipids to an air/liquid interface is required.

As stated previously, it is believed that the addition of neutral lipids, in the form of triglycerides or sterols, to the phospholipid compositions appear to stabilize the interaction of the composition with the interface surface. This stabilization effect is most readily demonstrated by, for example, both a maximized decrease in surface tension and an accelerated rate of surface-active lipid adsorption (indicated by an enhancement in surface hydrophobicity) greater than those induced by compositions which include only phospholipids. The mechanism by which neutral lipids and/or sterols potentiate phospholipid adsorption remains unclear.

In the investigation of this phenomenon, Applicant has utilized the method of surface pressure analysis by dynamic compression originally developed by Langmuir (*J. Am. Chem. Soc.* 38:2221-2295 (1916). In vitro transport studies revealed that the addition of a triglyceride (i.e., TP) to phospholipid mixtures markedly accelerated the adsorption of the surface-active molecules to the air/liquid interface with a greater lowering of surface-tension within the first 5 minutes post-administration, compared with values obtained 24 hrs after the administration of DPPC alone. In one preferred embodiment, the addition of a sterol, such as cholesterol, to a mixture of unsaturated phosphatidylcholine and unsaturated triglyceride also markedly accelerated adsorption of surface active lipids to an air/liquid interface and maximally reduced surface tension.

II. Description of the Lipid Compounds

As noted, the present invention is directed to charged and neutral lipids in general, and more particularly, to phospholipids, sterols and triglycerides which are formulated into unique anti-ulcer compositions useful to inhibit or retard ulcerogenesis. These compositions are also useful to treat or reduce the incidence of Respiratory Distress Syndrome and generally as a surfactant-replacing composition. The phospholipids and triglycerides of the present invention generally fall into two categories depending on the nature of their aliphatic substitutions, i.e., whether saturated or unsaturated.

As used herein, a saturated phospholipid or triglyceride is one in which all of the aliphatic substitutions are saturated and thus do not contain c=c double bonds. Conversely, unsaturated phospholipids are triglycerides having at least one unsaturated aliphatic substitution defined as including one or more c=c double bonds.

The phospholipids of the present invention are characterized generally by the formula—

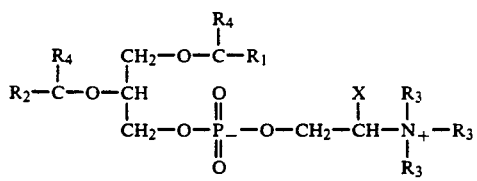

wherein $R_1$ and $R_2$ are saturated or unsaturated substitutions ranging from 8 to 32 carbon atoms; $R_3$ is H or $CH_3$, and X is H or COOH; and $R_4$ is $=O$ or $H_2$.

As will be appreciated by those of skill in the art, the foregoing chemical structure defines a zwitterionic phospholipid structure and embraces a wide range of phospholipids, including but not limited to phosphatidyl cholines, phophatidyl ethanolamines, phosphatidyl serines and various other zwitterionic phospholipids. A further listing of saturated and unsaturated fatty acid groups that can be esterified or ether-linked to the phospholipid in question can be found in Table 1. However, as will be appreciated, these listings are not intended to be a complete listing of useful phospholipids, and its inclusion herein is for the reader's convenience and to disclose Applicant's preferred embodiments.

Phospholipid compounds found to be particularly useful in the practice of the present invention are dilinoleoyl phosphatidylcholine (DLL-PC), dipalmitoyl phosphatidylcholine (DPPC) and egg phosphatidycholine (Egg-PC or $PC_e$). In DPPC, a saturated phospholipid, the saturated aliphatic substitution $R_1$ and $R_2$ are $CH_3-(CH_2)_{14}$, $R_3$ is $CH_3$ and X is H. In DLL-PC, an unsaturated phospholipid, $R_1$ and $R_2$ are $CH_3-(CH_2)_4-CH=CH-CH_2-CH=CH-(CH_2)_7$, $R_3$ is $CH_3$ and X is H. In Egg PC, which is a mixture of unsaturated phospholipids, $R_1$ primarily contains a saturated aliphatic substitution (e.g., palmitic or stearic acid), and $R_2$ is primarily an unsaturated aliphatic substitution (e.g., oleic or arachidonic acid).

The sterol compounds of the present invention are defined generally by the formula—

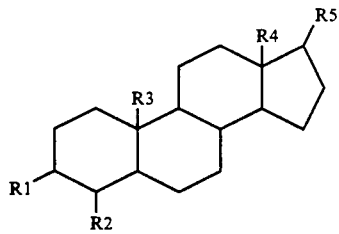

wherein the sterol contains zero, one or multiple double bonds in the perhydrocyclopentanophenanthrene ring; $R_1$ is either an H, O (ketone) or OH; $R_2$, $R_3$ and $R_4$ are either H or $CH_3$; and $R_5$ is a aliphatic chain (straight or branched) of between 1 and 14 carbon atoms in length.

The most common sterol included by this structure, and the one preferred for the preparation of the various sterol-containing compositions disclosed herein, is cholesterol. Cholesterol is typically preferred due to its ready availability, low cost and relative lack of toxicity or biological/hormonal activity. However, other sterols of this general structure may be employed where desired including, for example, beta-sitosterol, campesterol and desmosterol.

The triglycerides of the present invention are generally characterized by the formula—

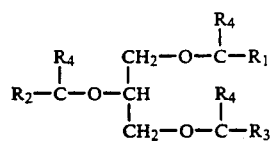

wherein $R_1$, $R_2$ and $R_3$ are each saturated or unsaturated substitutions ranging from 4 to 32 carbons atoms; and $R_4$ is either $=O$ or $H_2$.

As will be appreciated, this structure embraces a wide range of triglycerides, both saturated and unsaturated, and include, for example, triglycerides such as tripalmitin (saturated), triolein and trilinolein (both unsaturated). A further listing of saturated and unsaturated fatty acids that can be esterified or etherlinked to the triglyceride in question is displayed in Table I below. However, this table is included for convenience only and is merely representative of a variety of useful triglycerides and is therefore not intended to be inclusive.

TABLE I

FATTY ACIDS THAT MAY BE ESTERIFIED TO PHOSPHOLIPIDS AND TRIGLYCERIDES

| A. Saturated Fatty Acids | |
|---|---|
| n-Butyric acid (butanoic acid) | Stearic acid (octadecanoic acid) |
| n-Valeric acid (pentanoic acid) | Nondecylic acid (nonadecanoic acid) |
| Caproic acid (hexoic acid, hexanoic acid) | Arachidic acid (eicosanoic acid) |
| Enanthic acid (heptanoic acid) | Heneicosanoic acid |
| Caprylic acid (octanoic acid) | Behenic acid (dososanoic acid) |
| Pelargonic acid (nonanoic acid) | Tricosanoic acid |
| Capric acid (decanoic acid) | Lignoceric acid (tetracosanoic acid) |
| Undecylic acid (hendecanoic acid) | Pentacosanoic acid |
| Lauric acid (dodecanoic acid) | Cerotic acid (hexacosanoic acid) |
| Tridecylic acid (tridecanoic acid) | Heptacosanoic acid |
| Myristic acid (tetradecanoic acid) | Montanic acid (octacosanoic acid) |
| Pentadecylic acid (pentadecanoic acid) | Nonacosanic acid |
| Palmitic acid (hexadecanoic acid) | Melissic acid (triacontanoic acid) |
| Margaric acid (heptadecanoic acid) | Lacceroic acid (dotriacontanoic acid) |
| B. Unsaturated Fatty Acids | |
| trans-Crotonic acid (trans-butenoic acid) | $\Delta^{11}$-Eicosenoic acid |
| Iso-crotonic acid (cis-butenoic acid) | Cetoleic acid ($\Delta^{11}$-docosenoic acid) |
| $\Delta^3$-Hexenoic acid | Erucic acid (cis-$\Delta^{12}$-docosenoic acid) |
| $\Delta^4$-Decenoic acid (obtusilic acid) | Brassidic acid (trans-$\Delta^{13}$-docosenoic acid) |
| $\Delta^9$-Decenoic acid | Selacholeic acid (nervonic acid, cis-$\Delta^{15}$-tetracosenoic acid) |
| $\Delta^4$-Dodecenoic acid (linderic acid) | Ximenic acid ($\Delta^{17}$-hexacosenoic acid) |

TABLE I-continued
FATTY ACIDS THAT MAY BE ESTERIFIED TO PHOSPHOLIPIDS AND TRIGLYCERIDES

| | |
|---|---|
| $\Delta^5$-Dodecenoic acid (lauroleic acid) | Sorbic acid ($\Delta^{2,4}$-hexadienoic acid) |
| $\Delta^9$-Dodecenoic acid | Linoleic acid (cis-cis-$\Delta^{9,12}$-octadecadienoic acid) |
| $\Delta^4$-Tetradecenoic acid (tsuzuic acid) | Hiragonic acid ($\Delta^{6,10,14}$-hexadecatrienoic acid) |
| $\Delta^5$-Tetradecenoic acid (physeteric acid) | alpha-Eleostearic acid (cis-$\Delta^{9,11,13}$-octadecatrienoic acid) |
| $\Delta^9$-Tetradecenoic acid (myristoleic acid) | beta-Eleostearic acid (trans-$\Delta^{9,11,13}$-octadecatrienoic acid) |
| $\Delta^9$-Hexadecenoic acid (palmitoleic acid) | Linolenic acid ($\Delta^{9,12,15}$-octadecatrienoic acid) |
| cis-$\Delta^6$-Octadecenoic acid (petroselinic acid) | Stearidonic acid (moroctic acid $\Delta^{4,8,12,15}$-octadecatretraenoic acid) |
| Oleic acid (cis-$\Delta^9$-octadecenoic acid | Timnodonic acid ($\Delta^{4,8,12,15,18}$-eicosapentaenoic acid) |
| Elaidic acid (trans-$\Delta^9$octadecenoic acid | Arachidonic acid ($\Delta^{5,8,11,14}$-eicosatetraenoic acid |
| trans-Vaccenic acid trans-$\Delta^{11}$-octadecenoic acid) | Clupanodonic acid ($\Delta^{4,8,12,15,19}$-docosapentaenoic acid) |
| cis-Vaccenic acid (cis-$\Delta^{11}$-octadecenoic acid) | Nisinic acid ($\Delta^{4,5,12,15,19,21}$-tetracosahexaenoic acid) |
| $\Delta^{12}$-Octadecenoic acid | Thynnic acid (hexacosahexaenoic acid) |
| Gadoleic acid ($\Delta^9$-eicosenoic acid) | |

III. Formulation and Administration of Anti-ulcer Compositions

As noted above, it has been found that not all phospholipid-containing compositions function with adequate efficacy to render them particularly useful pharmacologically. Through extensive experimentation, Applicant has determined that while saturated phospholipids, for example, DPPC, exhibit a certain degree of antiulcer or ulcer preventative effect alone, the addition of a triglyceride (preferably saturated) to saturated phospholipid-containing compositions improves their activity to an amazing and unexpected degree.

Conversely, compositions which include only an unsaturated phospholipid, for example, Egg-PC or DLL-PC, show virtually no antiulcer activity alone. However, the addition of a sterol such as cholesterol surprisingly renders such compositions very active. Moreover, the further addition of certain triglycerides, which may be either saturated or unsaturated, further enhances the activity of unsaturated phospholipid/sterol compositions.

It is also of interest to note that the activity of unsaturated phospholipid/sterol compositions is lost if the sterol employed contains an aliphatic ester at the 3-position in place of the OH group of ring A of the sterol moiety.

The method of formulation of the various antiulcer compositions does not appear to be particularly crucial. As noted, protective effect can be obtained, for example, by simple direct administration of the lipids to a selected luminal surface. However, for most applications it will generally be desirable to provide the lipids in the form of a colloidal or liposomal suspension of the selected composition in an pharmaceutically acceptable aqueous diluent. While virtually any pharmaceutically acceptable aqueous diluent may be employed, it has generally been found that a certain level of salt, for example in the form of isotonic saline has significant anti-ulcer activity. Further, small amounts of heavy metals (or other polyvalent cations) or anti-oxidant chemicals with the capability of scavenging free radicals can be added to the diluent to provide a lipid composition of greater anti-ulcer efficacy, stability and lumen-coating effectiveness.

Colloidal suspensions are typically formulated to achieve a concentration of about 0.5 to 20 grams total lipid for each final milliliter of aqueous suspension, or more preferably, between about 1 and about 5 mg/ml. Although the particular methodology is not critical, it is preferred to provide the selected weighed lipid components n a suitable container, and dissolving them in either chloroform or ether. In this manner, aliquots containing known amounts of the selected lipid or lipid mixtures may be added to the mixing container. Once the solution, the chloroform or either is evaporated off under a stream of nitrogen, and a known volume of the desired diluent is added to the container in suitable proportions to achieve the desired final concentration of lipids. The entire admixture is then vortexed or sonicated for several minutes (at temperatures up to and above the transition temperature of the lipid, generally 4°–50° C. to achieve the final colloidal suspension.

It has been determined that the aqueous lipid suspensions are stable and maintain their gastric protective activity for several months when stored in amber bottles at either 4° C. or room temperature. Alternatively, the formulated lipid suspension can be lyophilized (or freeze-dried) to a powder which can either be simply resuspended in the desired diluent before use or administered directly as powder, capsule or table. We have evidence that minimal activity of the lipid mixtures is lost during lyophilization intratracheal administration of the lipid mixture as a powder may have significant advantages in the treatment of RDS and associated respiratory diseases.

It will be appreciated that in certain aspects the foregoing formulation procedure resembles procedures employed in the art for liposomal preparation. However, there is no requirement that liposomes be made in order to achieve useful lipid compositions in accordance with the present invention. For example, disrupted or aggregated liposomes, or non-liposomal colloidal dispersions, appear to be at least as efficacious as intact liposomes The subject compositions amy also take the form of a microemulsion. This is particularly the case where there is a preponderance of neutral lipids proportionately to phospholipids in the composition.

It is stressed, however, that there is no requirement that liposomes be made in order to achieve useful lipid compositions in accordance with the present invention. For example, disrupted or aggregated liposomes, or non-liposomal dispersions, appear to be at least as efficacious as intact liposomes. Moreover, except in the case of unsaturated phospholipid-containing compositions, sterols should be excluded from the formulation. Thus, although sonication of the admixture is preferred for mixtures containing saturated triglycerides, simple vortexing or otherwise similarly agitating the mixture will be sufficient. It also should be emphasized that in the presence of triglycerides the lipid suspension readily portions with one fraction floating to the surface, another saying in suspension and a third sedimenting to the bottom. This suggests that the lipids have formed a number of contrasting physical structures including: large dense mutilamellar vesicles; liposomes; lipid aggregates; mixed micellas; stable fat globules, microemulsions or lipid sheets. All of the above physical forms have been observed in the suspensions under electron microscopic examination. Most of these physical forms, thus, would have little or no luminal space as would a classical liposomal structure. However, all such preparations generally exhibit equally high activity independent of the lipid structure formed.

Regardless of the particular preparation method employed or type of suspension obtained, a sufficient amount of lipid is administered to adequately cover the desired tissue or luminal surface. Generally, sufficient coverage is obtained for oral application to the stomach by administering 5 ml to 500 ml of a 0.1 to 10 mg lipid/ml suspension per application, depending on the particular lipid mixture and the severity of the disease being treated. However, as will be appreciated, dosages of the formulations are not known to be particularly limited by any toxicity problems.

In addition to being useful in treating or preventing gastric ulcer disease, it is contemplated that the present formulations will prove useful in the treatment of any number of ulcerative or degenerative processes of the luminal lining of the G.I. tract, particularly in those areas of the G.I. tract that rely on an intact hydrophobic barrier for normal function. As measured by the contact angle technique which measures the hydrophobic character of a surface (see, e.g., Hills et al. (1983) *Am. J. physiol.*, 244:G561), it has been found that long stretches of the G.I. lumen, including for example the lower bowel, stomach and esophagus, are naturally quite hydrophobic. Such hydrophobic regions, and degenerative processes affecting such regions, are thus all candidates for beneficial therapy in accordance with the present invention. Moreover, specific ulcerative processes such as necrotizing enterocolitis and inflammatory bowel disease (e.g., ulcerative colitis and Crohn's disease) are believed to be amenable to hydrophobic treatment Other candidates include inflammatory processes such as inflammation of the esophagus (esophagitis). It has been found that many inflammatory processes are accompanied by decreases in the hydrophilic character of the affected tissue. In that it is postulated that this hydrophobic character serves to protect the underlying epithelium from injury, infections and inflammation, it is proposed that by maintaining the hydrophobic character of the tissue surface through the application of the present formulations, the protective barrier is reinforced.

Other related applications include application to the epidermal, vaginal or corneal epithelium as a method for treating inflammation or ulceration in these respective tissues. Moreover, due to the highly water impermeable and hydrophobic character of the urinary bladder, and the fact that a reduction in these properties can predispose the bladder to infection, it is proposed that the present formulations will prove beneficial in treating or preventing bladder infections.

IV. EXAMPLES ILLUSTRATING PREFERRED EMBODIMENTS OF ANTI-ULCER COMPOSITIONS

The following examples are representative experiments which have been included herein to illustrate Applicant's preferred embodiments. Most of the experiments were conducted in an experimental system designed to compare the ulcer protective efficacy of various lipid preparations versus saline controls. In this system, unless otherwise indicated, rats were intragastrically treated with 1 ml of a lipid test solution, generally at a total lipid concentration of 3-5 mg/ml, 2 hours before intragastric challenge with 1 ml of 1.0 N HCl or 100% ethanol. The rats were sacrificed 1 hour later at which time the lesion length resulting from the chemical challenge was measured in a blind or double-blind fashion.

These experiments therefore provide a model for directly comparing the activity of the various ulcer-protective compositions, and further, provide a reasonable basis from which to determine their relative ulcer-protective efficacy and dosages in humans. In addition, a set of experiments is included to demonstrate the ability of the present compositions to maintain the hydrophobicity of the liminal lining upon ulcerogenic challenge. The correlation between the ulcer-protective and hydrophobicity-maintaining activities of the compositions therefore becomes readily apparent.

For the following experiments, the following protocols were utilized for the preparation of lipid suspensions. The selected phospholipids, triglycerides and/or sterols were weighed in a screw cap vial and then dissolved in about 5 ml. chloroform. The chloroform was then evaporated under a stream of $N_2$ gas at room temperature. An amount of a solution of 0.86% NaCl in distilled water (pH 7.0) was then added which was sufficient to provide the final selected concentration. For mixtures of saturated phospholipids with saturated triglycerides (e.g.—DPPC+TP) and unsaturated phospholipids+sterol saturated triglycerides (e.g. —DLL—PC=Chol+TP), the mixtures were then sonicated for 5 minutes at room temperature. For compositions of a unsaturated phospholipid+sterol+unsaturated triglyceride (e.g. —$PC_e$+Chol+TO), the mixtures were vortexed for 2 minutes at room temperature. Additionally, for lipid mixtures which included a triglyceride, the mixture was capped under an $N_2$ environment prior to agitation.

The contact angle test was employed to compare and illustrate the ability of the three principal lipid composition embodiments to maintain the hydrophobic character of the liminal lining upon ulcerogenic challenge with one of three ulcerogenic agents, 1.0N HCL, 100% ethanol and 10% acetic acid (the latter administered to the colonic epithelium by enema). The tests were performed basically as described in Hills et al. (1983), *Am. J. Physiol.*, 244:G561, except using rat oxyntic (or colonic) tissue. The contact angle test relies on the finding that the contact angle subtended between a droplet of aqueous fluid and a nonwettable surface provides a direct estimation of the degree of hydrophobicity of the surface.

Hydrophobicity is characterized by any tendency of a fluid to form beads on the surface rather than to spread evenly. A quantitative index for this phenomenon is obtained by measuring the contact angle. This is the angle between the solid-liquid and liquid-air interfaces at the triple point where solid, liquid, and air meet. It can vary from 0° for water on a particularly hydrophobic surface such as Teflon.

In the present experiment, a section of rodent oxyntic (or colonic tissue (5×15 cm) was carefully excised, laid flat, and gently wiped free of gastric contents and mucus. The mucosal surface was then lightly rinsed with saline before being transferred to the flat horizontal stage of a goniometer, which is the standard instrument for measurement of any contact angle. Any excess rinse solution was removed by gentle blotting, and the tissue was stabilized at 25° C. for 5 min.

Contact angle is a basic surface parameter and one very commonly measured on human skin by cosmetic chemists. The standard equipment for its determination is a goniometer (Rame-Hart model 100-00 115) fitted with a monochromatic light source, camera attachment, and micrometer-activated syringe (Rame-Hart 100-10) for applying small volumes of saline to either the treated or control tissue surfaces. Five microliters of normal saline were applied to the liminal surface of the tissue and the contact angle was measured in the standard way.

The center of the field of view was adjusted to coincide with the triple point, and then one cross hair was adjusted to coincide with the tissue-fluid interface and the other to present a tangent to the liquid-air interface. The angle between the two is the contact angle and can be read off directly from the scale encircling the eyepiece. Magnification (×25) of the triple point enables the observer to allow for tissue irregularity in measuring contact angle. The effects of micro irregularities is a subject of discussion among physicists, but he macro value is still a good reflection of the micro value. Contact-angle determinations were repeated at two or more other sites on the sample, all within the oxyntic (or colonic region of the mucosa.

EXAMPLE

Contact Angle Studies

For the results displayed in Table II, the three general embodiments of lipid compositions were employed to demonstrate their ability to protect the "contact angle" (i.e., hydrophobicity) of the rat oxyntic tissue upon ulcerogenic challenge. The three exemplary combinations comprised 2) a saturated phospholipid and saturated triglyceride (DPPC-TP); 2) an unsaturated phospholipid, a sterol saturated triglyceride (DLL-PC-TP; and 3) an unsaturated phospholipid, sterol and unsaturated triglyceride ($PC_e$CH-TP).

As shown in Table II, the two gastric ulcerogens, ETOH and HCl, were found to reduce the observed contact angle 1 hr after intragastric administration from an average of about 36° (control-untreated) to about 8° and 5° (control-treated), respectively. However, pretreatment with any one of the three lipid composition groups almost entirely reversed the effect of the ulcerogens. The DPPC-TP treatment was found to provide the most effective barrier to hydrophobic erosion, with DLL-PC-TP and $PC_e$CH-TO providing a reduced but nevertheless effective barrier.

TABLE II

CONTACT ANGLE[a] MAINTENANCE BY MIXTURES OF POLAR AND NON-POLAR LIPIDS

| Challenge-Test 1h Soln | PRETREATMENT | | | |
|---|---|---|---|---|
| | Saline | $PC_e$-CH—TO | DLL—PC—TP | DPPC—TP |
| Saline | 36.2 ± 0.8 (control) | 38.0 ± 0.9 | 46.3 ± 4.2 | 39.9 ± 0.8 |
| 100% ETOH | 8.3* ± 2.2 | 25.5** ± 3.2 | NT | 37.0** ± 2.7 |
| 1.0 N HCL | 5.2* ± 2.8 | 27.9** ± 1.7 | 30.9** ± 2.7 | 36.0** ± 1.3 |

[a]Values are mean ± SEM of gastric contact angles (degrees) measured at sacrifice. 3 hrs after pretreatment and 1 hr after challenge.
Abbreviations: NT = Not tested; ETOH = ethanol; $PC_e$CH—TO = Mixture of egg Phosphatidylcholine + 50 M% cholesterol (1 mg/ml) + Triolein (4 mg/ml); DLL—PC—TP = Mixture of Dilinoleoyl Phosphatidylcholine + 80 M% cholesterol (1 mg/ml) + Tripalmitin (10 mg/ml); DPPC—TP = mixture of dipalmitoyl Phosphatidylcholine (1 mg/ml) + Tripalmitin (4 mg/ml).
* = $p < 0.05$ vs contact angle values of controls (saline pretreated, saline challenged). ** = $p < 0.05$ vs. contact angle of rats pretreated with saline and challenged with either 100% ETOH, or 1N HCl.

EXAMPLE 2

Lesion Length Studies

Referring now to FIG. 1 is shown the first of a series of experiments employing the reduction in lesion length test system as an indication of ulcer protective action. In the FIG. 1 experiment, the ulcer protective activity of various combinations of an unsaturated phospholipid, Egg PC ($PC_e$), and a sterol (cholesterol) were compared to a saline control. In these experiments, 1 ml of the lipid solution was intragastrically administered to rats two hours before the animals were challenged with 1 ml of 1N HCl. The rats were sacrificed 1 hr later at which time lesion score was quantified.

As will be readily appreciated from FIG. 1, although neither $PC_e$ nor cholesterol were found to protect against acid-induced gastric lesions on their own, combination of the agents ranging between 60 and 20 mole % cholesterol (i.e., between 40 and 80 mole % $PC_e$) were found to provide a strong and unexpected protection to the stomach. A maximum of 85% reduction in lesion length was observed with a 50/50 mole % mixture of cholesterol and $PC_e$.

In FIG. 2, a similar experiment was performed with a composition containing dilinoleoyl phosphatidyl choline (DLL-PC) and cholesterol. In this experiment, it was found that a similar range of molar percentages provided roughly similar activity. However, in this case, a maximal reduction in lesion length of 85% was observed with a mixture of 20 mole % DLL-PC and 80 mole % cholesterol.

FIG. 3 illustrates the long-lasting ulcer protective action of the most preferred combinations from the FIG. 1 and 2 experiments. Here it was demonstrated that both combinations, $PC_e$+50% Chol and DLL-PC+80% Chol, were both capable of maintaining protective activity if administered either 2 or 4 hrs prior to the acid challenge. Moreover, $PC_e$+50% Chol. was found to provide some protection even at 6 hours post-administration.

Figure 4:
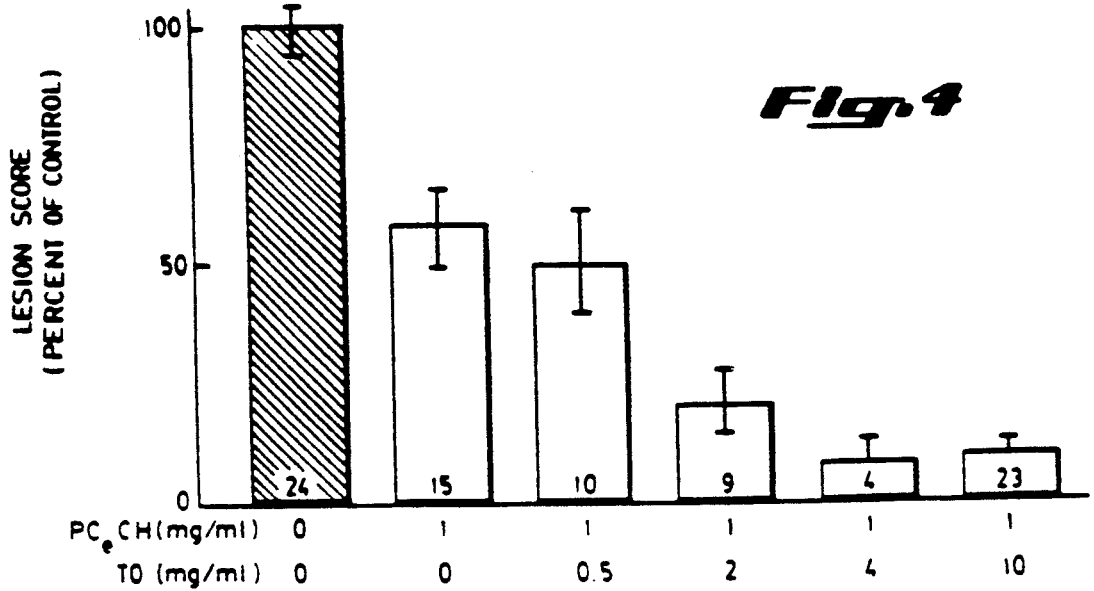
FIG. 4. This figure demonstrates that the protective action of a lower dose (1 mg/ml) of the $PC_e$+50 M% Chol ($PC_e$ CH) mixture (to approximate the $ED_{50}$) could be significantly enhanced in a dose dependent fashion by the addition of the triglyceride, triolein (TO)< to the mixture. Although not shown here, TO on its own (10 mg/ml) had only a small protective action (<20% reduction in lesion score) against acid-induced lesions.
Figure 5:
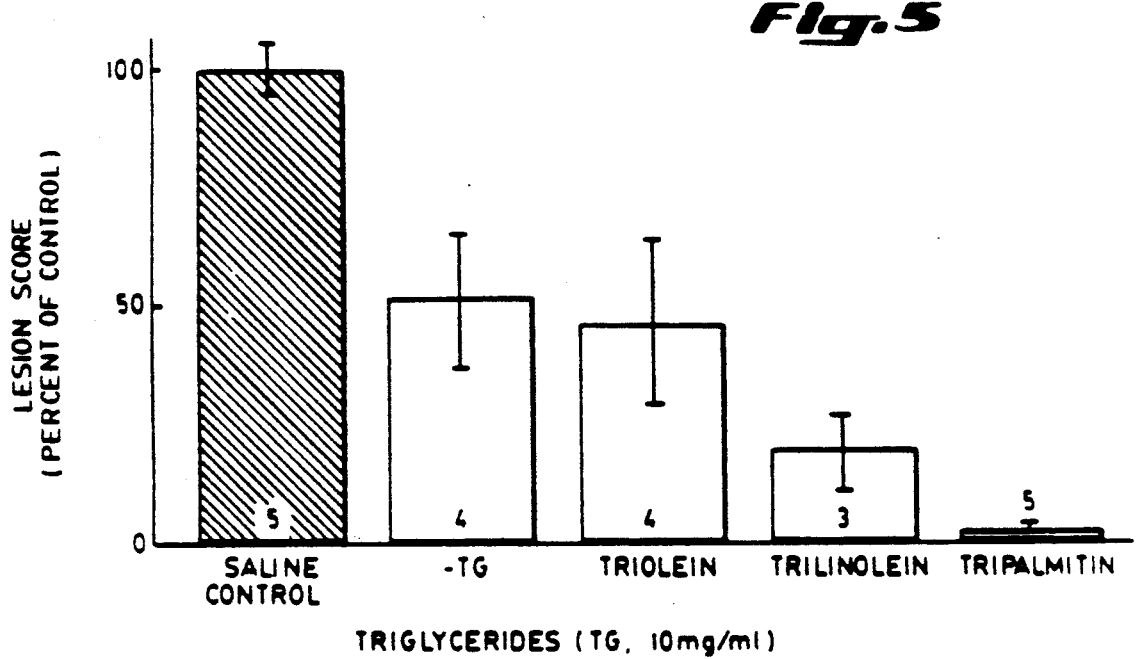
FIG. 5. Effect of different triglycerides (TG) on protective action of lipid mixtures of dilinoleoylphosphatidylcholine and 80M% cholesterol (DLL-PC-CH) against acid-induced gastric lesions. This figure graphically illustrates that the addition of Tripalmitin and Trilinolein to an $ED_{50}$ dose (1 mg/ml) of the DLL+80 M% Chol mixture enhanced the protective efficacy of the suspension, whereas addition of TO to the mixture was only minimally effective.

In FIGS. 4 and 5, the ulcer-protective efficacy of unsaturated phospholipid/cholesterol combinations are shown to be surprisingly enhanced upon the inclusion of a triglyceride, triolein (TO), in a 1 mg/ml combination of $PC_e$ and 50 mole % cholesterol ($PC_e$CH) greatly improved its efficacy. A maximum reduction in lesion length of >90% was observed with the combination of 1 mg/ml PC$_e$CH and 4 mg/ml TO.

In FIG. 5, a similar experiment is shown for the combination of dilinoleoyl phosphatidylcholine and 80 mole % cholesterol (DLL-PC-CH) with each of three different triglycerides. Two of the triglycerides employed, triolein (TO) and trilinolein (TL), were unsaturated triglycerides, while the third, tripalmitin (TP), was a saturated triglyceride. The DLL-PC-CH was employed at its ED$_{50}$ (1 mg/ml) with the various triglycerides being included at 10 mg/ml. As will be appreciated from the data displayed in FIG. 5, tripalmitin was found to be the most efficacious triglyceride additive, with an observed reduction in lesion length of about >95%. Triolein was found to be the least effective triglyceride additive, with trilinolein somewhere in between.

EXAMPLE 3

Sterol Esterification Studies

In a series of experiments represented by Table III below, the effect of esterification of cholesterol at carbon position 3 on the ulcer protective activity of DLL-PC was investigated. In general, the results indicated that cholesterol esters of this type were not capable of lending any gastric protective effect to DLL-PC.

Figure 12:
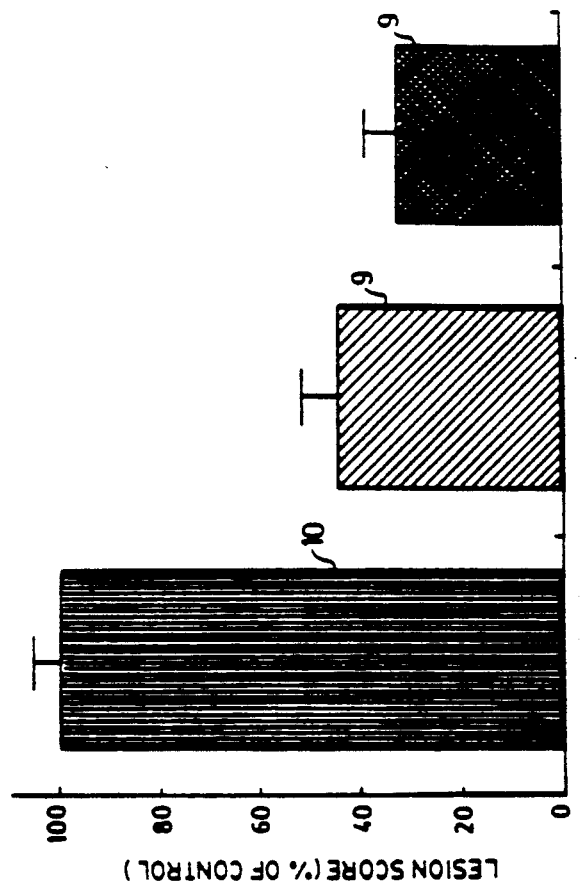
FIG. 12. Protective effect of mixtures of unsaturated phospholipids: sterols and triglycerides (specifically $PC_e$:CH:TO) is present if cholesterol (CH) is substituted for equimolar amounts of the plant sterol, beta-sitosterol.
Figure 11:
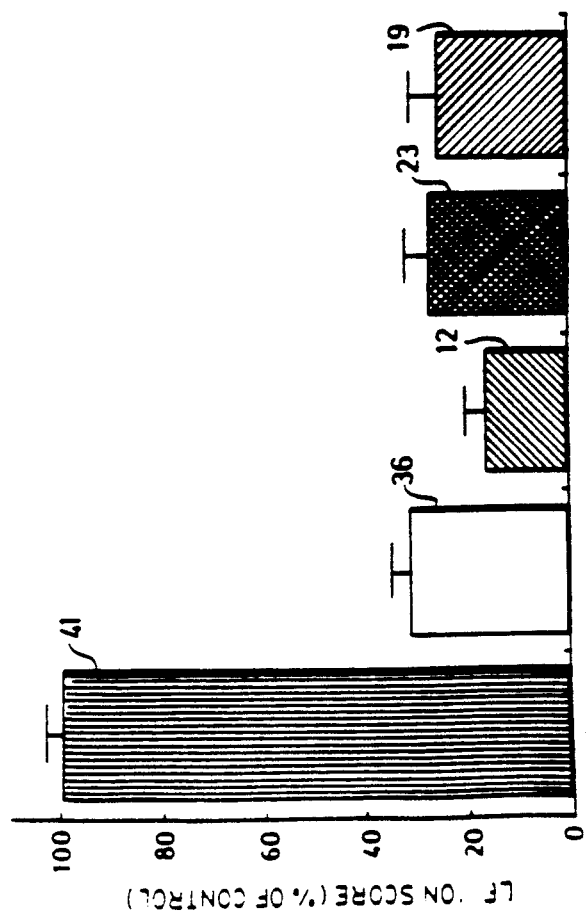
FIG. 11 Protective effect of DPPC-TP mixture (administered 2 hours before challenge) against acid-induced gastric lesions is present if one or both of the ester lipids is substituted by inert ether analogues. Abbreviations: TPE=Tripalmitin ether; DPPCE=Dipalmitoyl phosphatidylcholine ether.

Additionally, Applicant has demonstrated that the use of beta-sitosterol may be substituted for cholesterol in the subject phospholipid compositions without loss of the compositions protective efficacy. For example, FIG. 12 it is demonstrated that in lipid mixtures of unsaturated phospholipid sterol and unsaturated triglycerides, the plant sterol, beta-sitosterol can be readily substituted in equimolar amounts for cholesterol with equal protective activity against acid-induced lesions (Lipid mixtures administered 2 hrs before acid challenge). These results suggest that sterols which have minimal ability to form atherosclerotic plaques and thus cardiovascular side-effects such as beta-sitosterol may be a desirable alternative sterol to use clinically in these mixtures.

TABLE III

Effect of Cholesterol and Cholesterol Esters[a] on Gastric Protective Effect of Lipid Suspensions of Dilinoleoyl-Phosphatidylcholine (DLL—PC) Against Acid-Induced Lesions

| Pretreatment Test Solution | n | Lesion Score (% of control) |
|---|---|---|
| Saline | 10 | 100 ± 9.4 |
| DLL—PC + Cholesterol | 3 | 28.1 ± 1.7* |
| DLL—PC + Cholesteryl-arachidonate | 3 | 92.8 ± 13.2 |
| DLL—PC + Cholesteryl-n-butyrate | 5 | 109.0 ± 11.9 |
| DLL—PC + Cholesteryl-linoleate | 4 | 118.3 ± 20.8 |
| DLL—PC + Cholesteryl-oleate | 4 | 83.8 ± 13.4 |
| DLL—PC + Cholesteryl-palmitate | 5 | 74.8 ± 12.1 |

[a]Cholesterol or cholesterol esters added at a conc. on 80 M % (total lipid conc. = 3 mg/ml).
[b]Gastric lesion induced by the intragastric administration of 1 ml of 1N HCl two hrs after they have been pretreated with 1 ml of either saline (controls) or the liposomal test solutions. Animals were sacrificed 1 hr after acid-challenge.
* = p <0.05 vs lesion score of controls.

EXAMPLE 4

Effect of the Addition of a Triglyceride and /or Sterol to a Phospholipid

Figure 6:
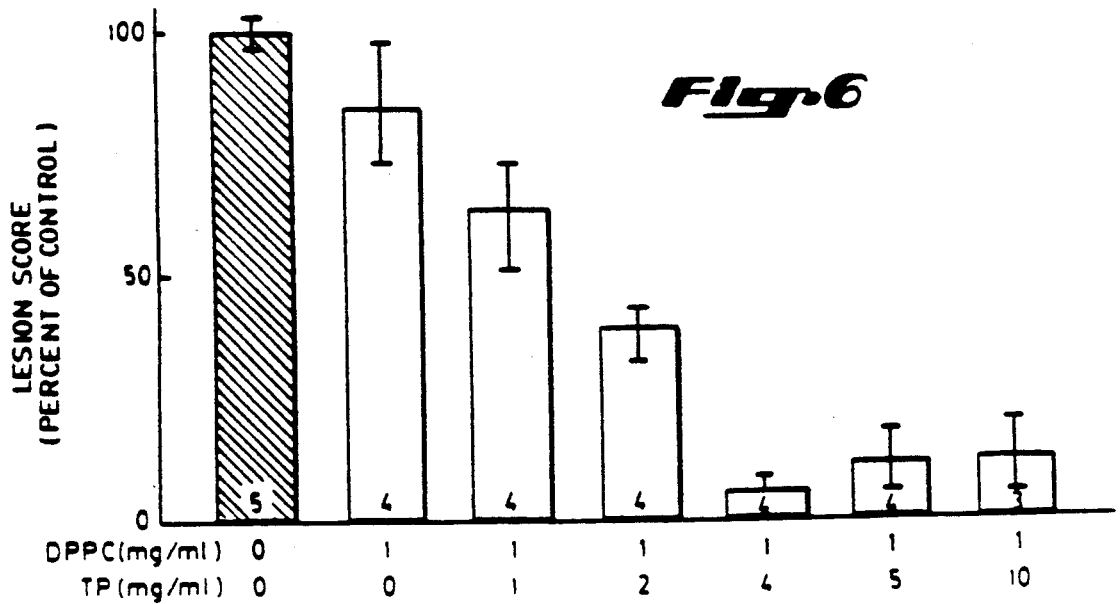
FIG. 6. Dose-dependance of Tripalmitin (TP) on the protective effect of mixtures of dipalmitoyl-phosphatidylcholine (DPPC) against acid-induced gastric lesions. This figure demonstrates that the protective action of low doses of DPPC mg/ml) could be enhanced in a dose dependent fashion by the addition of Tripalmitin (TP) to the mixture. Although not shown here TP on its own (10 mg/ml had only a modes protective action, reducing lesion score by greater than 30%.

In FIG. 6, the gastric protective activity of compositions including a saturated phospholipid, DPP, together with a saturated triglyceride, TP, is disclosed. As will be appreciated, some protective effect was observed with the saturated phospholipid alone in that DPPC alone at 1 mg/ml was capable of providing a reduction in lesion length of about 10%. However, the inclusion of varying concentrations of a saturated triglyceride greatly enhanced the activity of DPPC. The most profound effect was obtained with compositions of 1 mg/ml DPPC together with 4 mg/ml TP, at which concentration a greater than 95% reduction in lesion length over control was observed.

Figure 7:
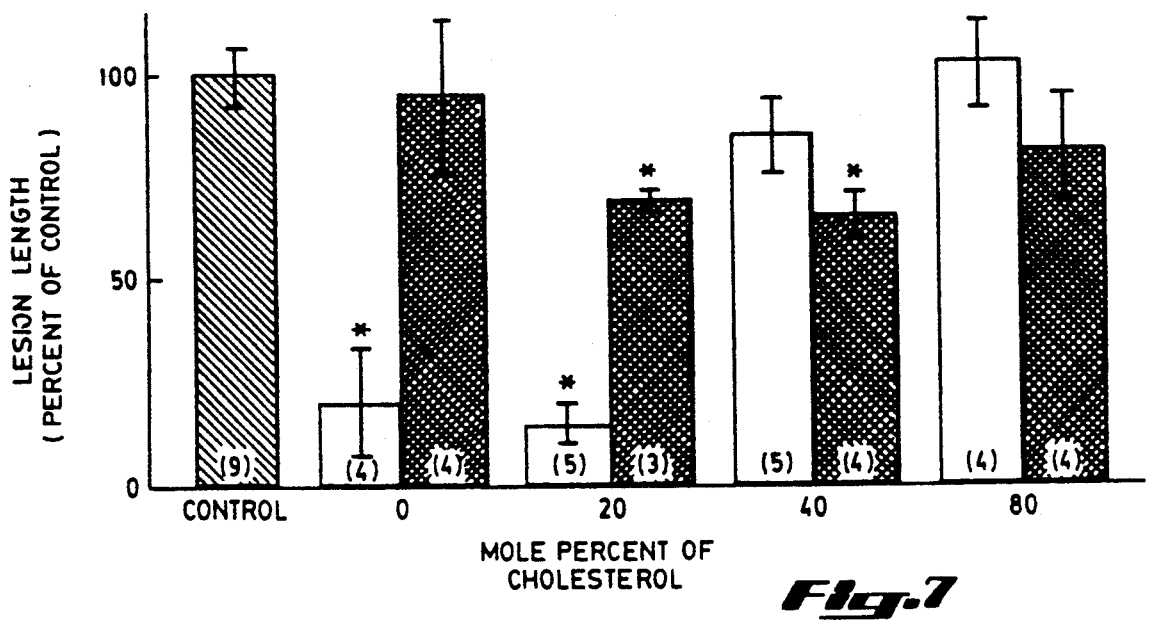
FIG. 7. The data presented here show that in contrast to the ability of Chol to augment the protective action of the unsaturated phospholipids, $PC_e$ and DLL-PC, addition of Chol to liposomes of the saturated phospholipid, DPPC, either had no effect (1 mg DPPC/ml) or in fact, inhibited the protective efficacy of higher concentrations of DPPC (3 mg. DPPC/ml).

Although, in general, saturated phospholipids alone, as observed in FIG. 6, were capable of providing a protective effect, it was found that the addition of increasing amounts of cholesterol to saturated phospholipid preparations progressively reduced their observed activity. These data are displayed in FIG. 7. In particular, when cholesterol was added to a 3 mg/ml preparation of DPPC (ED$_{50}$ dose) at mole % ratios of greater than 20 mole %, the protective activity of DPPC was lost. This therefore demonstrates that cholesterol should not be included in lipid compositions based on saturated phospholipids.

Figure 8:
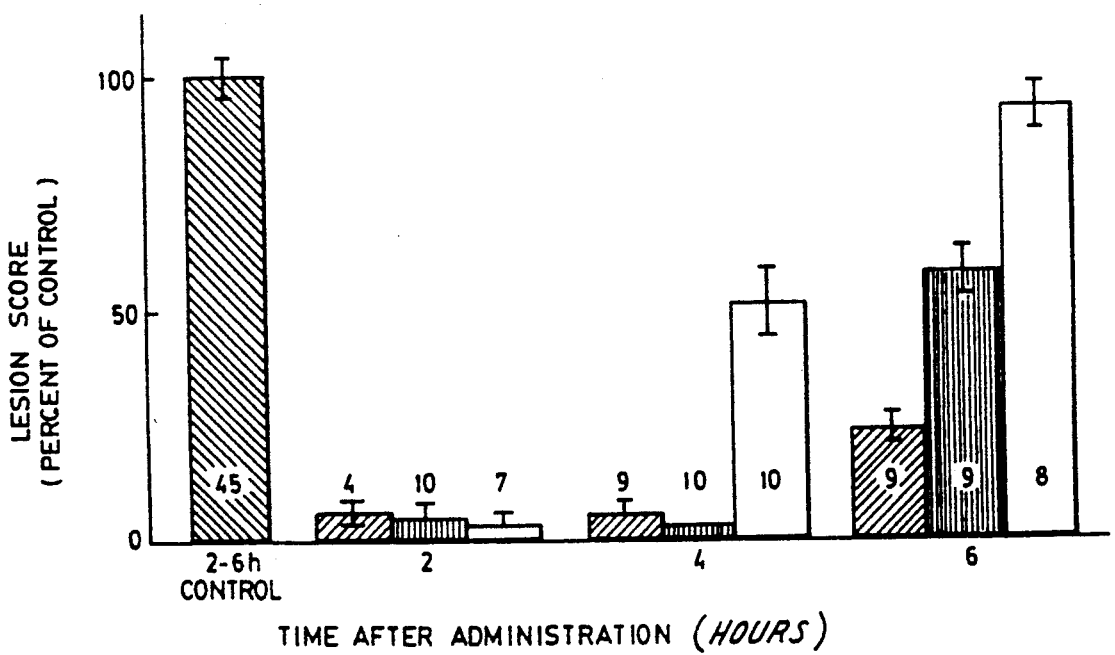
FIG. 8. Time-dependance of protective effect of mixtures of polar and non-polar lipids against acid-induced gastric lesions. this figure demonstrates that in addition to enhancing its efficacy, addition of the triglycerides (TG) to the mixtures of lipids appeared to prolong their duration of action [i.e. at 6 hrs—$PC_e$+50 M% Chol+TO still reduced lesion score by 75%, whereas in the absence of the TG (See FIG. 3) it only reduced lesion score by 25%—6 hrs after administration].
Figure 10:
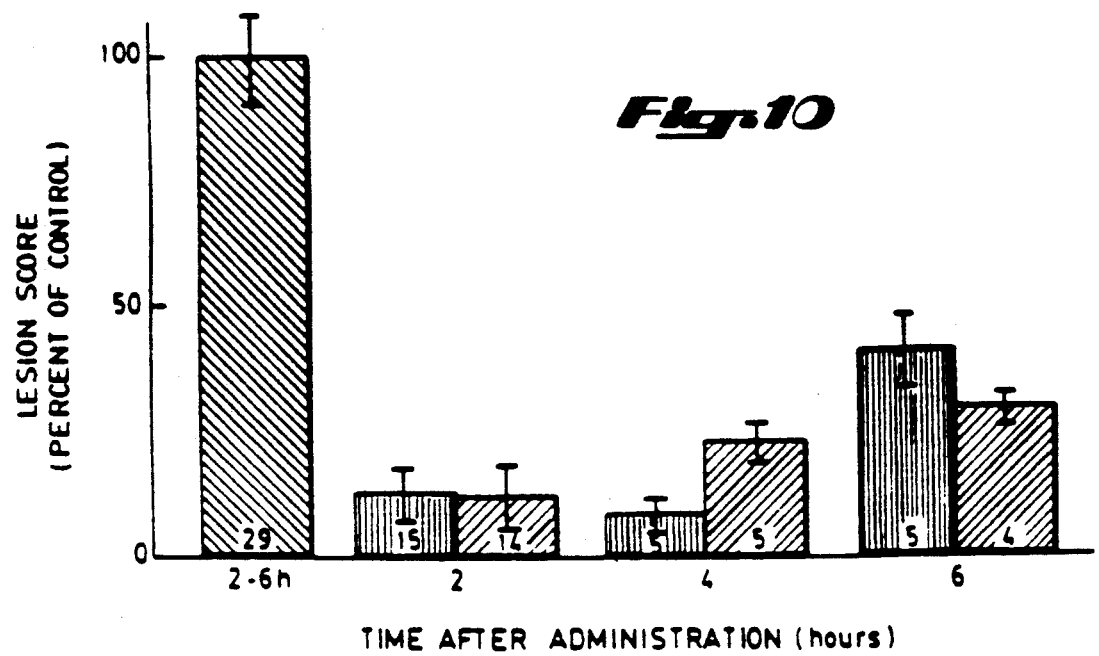
FIG. 10. Time-dependance of protective effect of mixtures of polar and non-polar lipids against ethanol-induced gastric lesions. This figure demonstrates that similar to the protective against acid-induced damage, the protective action of two mixtures against ethanol-induced gastric injury was long acting and still provided significant protection 6 hrs after administration.

FIGS. 8 and 10 represent experiments directed at comparing various aspects of the relative activity of the three general embodiments of the invention. In FIG. 8, the time-dependance of the protective effect of the three embodiments against acid-induced lesions is compared. As displayed therein, all three preferred embodiments gave very profound protective effect as of two hours post-administration. By 4 hours, the combination of unsaturated phospholipid+sterol+saturated triglyceride (DLL-PC+Chol+TP) was found to be somewhat less active, but active nevertheless. The combinations of unsaturated phospholipid+sterol+unsaturated triglyceride (P$_e$+Chol+TO) and saturated phospholipid+saturated triglyceride (DPPC+TP) were found to retain virtually total activity at 4 hours. By six hours, the DLL-PC+Chol+TP treatment was almost devoid of activity, while the remaining combinations were still providing a significant degree of protection.

Figure 9:
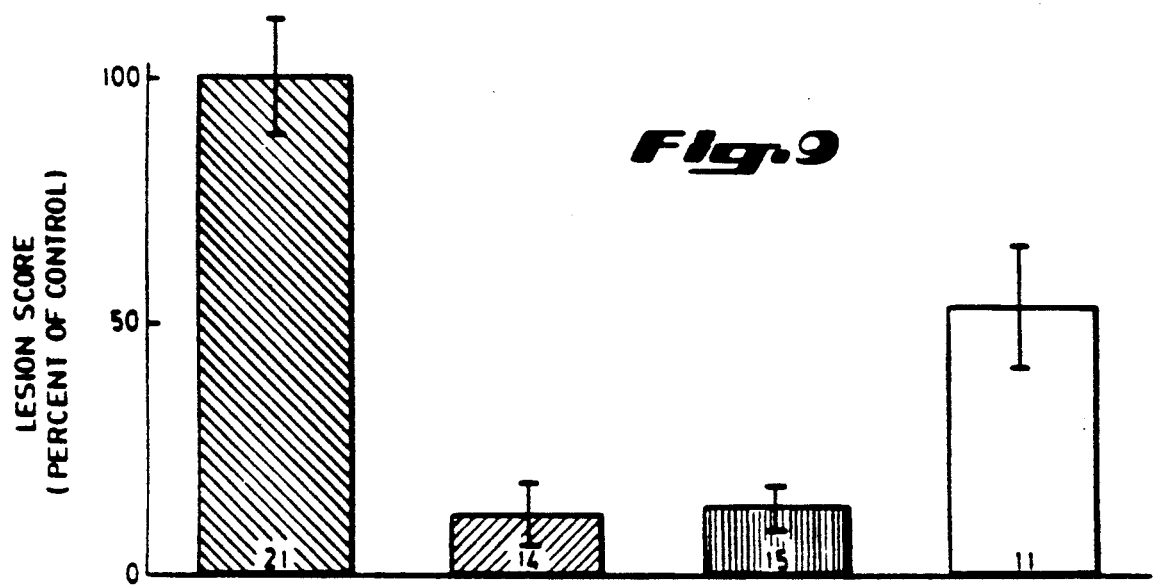
FIG. 9. Protective effect of mixtures of polar and non-polar lipids against ethanol-induced gastric lesions. This figure demonstrates that mixtures of phospholipids/Chol/TG had profound protective action against another gastric ulcerogenic challenge, intraluminal administration of 1 ml of 100% ethanol. As before, lipid mixtures were administered 2 hrs before challenge and the rats sacrificed 1 hr after challenge.

In FIG. 9, the direct protective effect of the same combinations against ethanol-induced gastric lesions were compared, with the combinations of unsaturated phospholipid+sterol+unsaturated triglyceride and saturated phospholipid+saturated triglyceride both exhibiting an almost equally high protective activity. While the unsaturated phospholipid+sterol saturated triglyceride was found to be the least effective, it nevertheless exhibited significant activity.

EXAMPLE 5

Time-Dependence and Stability Studies

In FIG. 10, the two most active lipid combinations were tested for the time-dependance of their protective effect against ethanol induced gastric lesions. As will be appreciated, both combinations exhibited excellent protective activity up through 6 hours post administration.

The present compositions were also studied to determine their protective efficacy after either lyophilization or storage in amber bottles at room temperature. Each rat was treated with one of the aged phospholipid combinations described in FIG. 19 and a chemical challenge of HCl administered. As demonstrated in FIG. 19, compositions of DPPC+TP and $PC_e$+Chol+ascorbic acid provided effective ulcerogenic protection up to 55 days after formulation. In contrast, mixtures of DPPCE+TP provided a sustained level of ulcerogenic protection only up to 41 days after formulation. All mixtures lost significant amounts of ulcerogenic protective capacity 113 days after formulation.

Applicant also conducted studies on the proective efficacy of various lyophilized lipid mixtures stored at room temperature over various periods of time. The various lipid compositions shown in FIG. 20 were prepared in accordance with procedures previously described in the specification. Thereafter, each composition was lyophilized according to procedures well known to those of skill in the art. The lyophilized compositions were then administered to a adult rats in the form of a power being "blown" onto the gastric mucosa. An HCl gastric challenge was then administered to each rat. The lesion score produced in each animal after such a challenge was then expressed as a % of control lesionary (i.e. saline treated).

Figure 20:
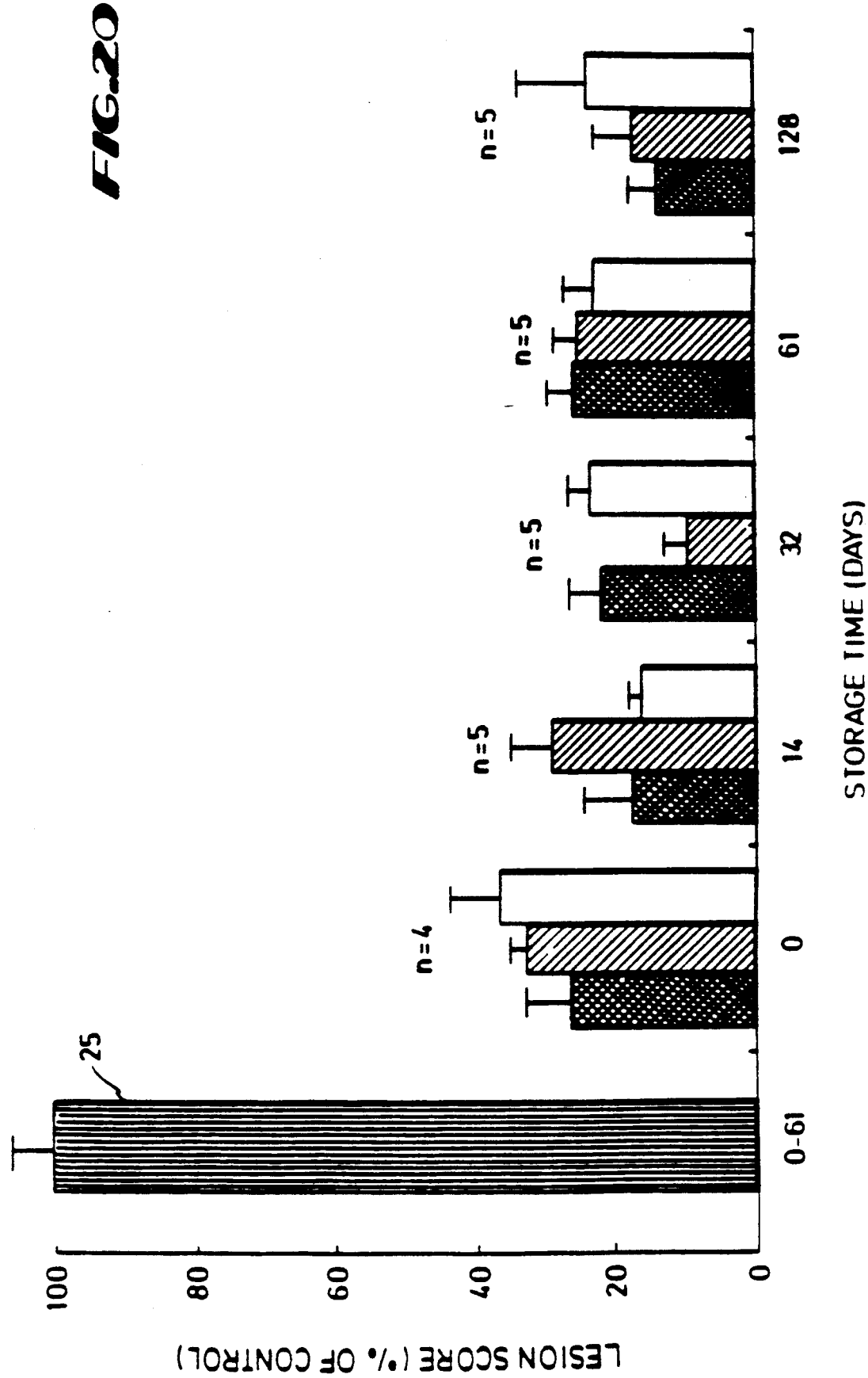
FIG. 20. The protective efficacy of lyophilized lipid mixtures, stored over a period of time at room temperature, against 0.75 N HCl challenge in adult rats.

As demonstrated at FIG. 20, the various lipid compositions remained stable and retained their protective efficacy up to 128 days after lyophilization. No significant difference between the protective efficacy of each composition was demonstrated. For example, the lyophilized compositions were able to effect less than 40% lesion score for all lipid compositions up to 128 days after lyophilization, in contrast to the 90% lesion score obtained in animals treated with 113 day old non-lyophilized lipid compositions. These results suggest that lyophilization of a phospholipid composition will preserve the protective efficacy of that composition for a longer period of time compared to non-lypholized phospholipid compositions.

EXAMPLE 6

Effect of Polyvalent Cations and Anti Oxidants to Lipids

In a series of experiments represented by Tables V and VI, the effect of the addition of either polyvalent cations or anti-oxidants (vitamins) to a phospholipid composition on the protective efficacy of the composition were investigated. In each of the studies, groups of adult male rates were pretreated 2 hours before gastric chemical challenge with the particular phospholipid composition. A chemical challenge of HCl was then administered as previously described. The animals were sacrificed 1 hour after acid challenge and gastric lesion measured.

(a) Polyvalent Cations

In Table V it is shown that low (threshold)0 does of the lipid mixtures alone achieved only minimal reduction in lesion score. However, the addition of a polyvalent cation in the form of 0.2 mM $AU^{+++}$ ions resulted in a dramatic potentiation in the lipid mixtures protective efficacy. Other experiments have demonstrated that aluminum ($AL^{+++}$) bismuth ($Bi^{+++}$) and calcium ($Ca^{+++}$) 0 have similar potentiation activity.

TABLE V

Ability of Gold Salts[a] ($Au^{+++}$) to Enhance the Protective Effect of Lipid Mixtures Against Acid-Induced Gastric Ulcerogenesis

| Pretreatment | No. of Rats group | Lesion Score[d] (% of control) |
|---|---|---|
| Phosphate Buffer (control) | 5 | 100 ± 12 |
| $Au^{+++}$ (0.2 mM)[a] | 5 | 83.6 ± 7.6 |
| $PC_e$ + Chol + TO[b] | 5 | 44.8 ± 5.8 |
| $PC_e$ + Chol + TO + $Au^{+++}$ [b,a] | 5 | 29.6 ± 10.0 |
| DPPC + TP[c] | 5 | 65.1 ± 11.5 |
| DPPC + TP + $Au^{+++}$ [c,a] | 5 | 9.7 ± 2.7 |

[a]Chloroauric Acid (0.2 mM) was made up in phosphats buffer (0.1 M, pH 7.0).
[b]$PC_e$ + 50 M% Chol (0.5 mg/ml) + 2 mg/ml TO
[c]DPPC (0.5 mg/ml) + 2 mg/ml TP
[d]Gastric lesions were measured 1 hr after acid challenge and 3 hrs prior to pretreatment.

(b) Anti-oxidants

Similarly, Table VI reflects data from experiments conducted employing the lipid mixtures in combination with various anti-oxidants. The results demonstrate that, as with polyvalent cations, the addition of anti-oxidant vitamins potentiates the protective efficacy of the phospholipid composition.

TABLE VI

Ability of Lipid-and-Water-Soluble Vitamins with Anti-oxidant Activity to Enhance the Gastric Protective Efficacy of Mixtures of Egg-phosphatidylcholine ($PC_e$), Cholesterol and Triolein ($PC_e$ + Chol + TO) Against Acid-Induced Lesions

| Pretreatment | No. of Rats group | Lesion Score[d] (% of control) |
|---|---|---|
| Saline (control) | 4 | 100 ± 6.4 |
| $PC_e$ + Chol + TO[a] | 4 | 58.6 ± 6.9 |
| $PC_e$ + Chol + TO + Vit C[b] | 4 | 17.7 ± 3.3 |
| $PC_e$ + Chol + TO + Vit A[c] | 4 | 61.1 ± 10.5 |
| $PC_e$ + Chol + TO + Vit A, + Vit C[b,c] | 4 | 12.8 ± 9.6 |

[a]$PC_e$ + 50 M % Chol (0.3 mg/ml) + 1.2 mg/ml TO.
[b]Vitamin C added at a final conc. of 20 mg/ml
[c]Vitamin A added to lipid in chloroform at a final conc. of 1 mg/ml
[d]Gastric lesione were measured 1 hr after acid-challenge and 3 hrs prior to pretreatment This clear potentiative effect of the polyvalent cations and antioxidants with the lipid mixtures was indeed a surprising finding since at the concentrations employed neither gold salts nor vitamins A and C had any gastric protective activity on their own.

EXAMPLE 7

Comparative Inflammatory Bowel Disease Studies

To demonstrate the applicability of the present lipid compositions in the treatment of other gastrointestinal lesions, they were tested in an animal model designed to mimic the pathological changes associated with inflammatory bowel disease. In these experiments, the hydrophobicity of the colonic mucosa of rats was measured 5 days after the animals were administered enemas (0.5 ml) containing either saline (control) or 10% acetic acid (30 second rinse). It has been demonstrated in the scientific literature that administration of acetic acid y this route results in erosive and inflammatory changes in the colonic mucosa which resembles the pathological changes associated with inflammatory bowel disease.

In experimental rats, 0.5 ml of each of the three lipid mixtures (DPPC-TP, DLL-PC-Chol-TP, $PC_e$-Chol-TO) was administered 2 hrs prior to and immediately following the acetic acid rinse. The results shown in Table VII below indicate that the rodent colonic mucosa is quite hydrophobic under control conditions and this non-wettable property is significantly reduced in response to experimentally-induced colitis. However, this transition from a non-wettable to a wettable state was reversed when the rats were treated with the unique mixtures of polar and non-polar lipids.

TABLE VII

Surface Hydrophobicity of the Rodent Colonic Mucosa in Experimentally-Induced Colitis: Ability of Lipid Mixtures to Maintain This Protective Hydrophobic Property

| Group Pretreatment | Acetic Acid | No. of rats group | Contact Angles |
|---|---|---|---|
| Saline | — | 3 | 60.7 ± 14.8° |
| Saline | + | 3 | 38.0 ± 3.2° |
| DPPC—TP | + | 4 | 79.8 ± 2.2° |
| PCe + Chol + TO | + | 3 | 67.7 ± 7.1° |
| DLL—PC—Chol + TP | + | 4 | 59.3 ± 12.0° |

EXAMPLE 8

Comparative Studies of Phospholipid Protection Against Various Ulcerogenic Agents The protective effect of various lipid mixtures were tested against different experimentally induced gastric ulcerogenesis agents in the rat. All rats were pretreated with 1 ml of lipid mixtures (5 mg/ml) or saline (controls) 2 hrs before ulcer challenge.

Table VIII demonstrates that different mixtures of polar and neutral lipids can all provide rats with marked protection against gastric ulceration induced by a number of different injurious conditions, including: ethanol, bile acid, aspirin, and stress-induced gastric lesions. In all cases except stress-induced ulcers, the rats were sacrificed 1 hr after receiving 1 ml of the ulcerogenic agent. Stress ulcers were induced by cold (4° C.) restraint in a restraining screen. These animals were sacrificed 4 hrs after being placed in the restraining screen.

As shown on Table VIII, the DPPCD+TP pretreatment was found to have the least protective effect against aspirin (10 mg/ml, pH 3.0), with the greatest protective effect being provided by a $PC_e$+CH+TO lipid pretreatment. The lowest lesion score was evidenced in the $PC_e$+CH+TO+Vit+C lipid pretreatment group upon challenge with bile sale (160 mM taurocholic acid in 0.2N HCl showing a lesion score of 5.8±3.3%.

V. Formulation and Administration of Surfactant Replacement Compositions

Over the past 10 years investigators and physicians have made great strides in the treatment of neonatal and adult Respiratory Distress Syndrome (RDS) by surfactant replacement therapy. However, the use of certain phospholipids important in lung surfactant composition remains of marginal therapeutic value. This is owing in part to the very slow rate at which certain phospholipids are adsorbed to an air/liquid interface. Through extensive experimentation, Applicant has found that the addition of a triglyceride (preferably saturated) to a surface-active phospholipid containing composition improves the rate of phospholipid adsorption and augments potential surface tension effects significantly.

Conversely, compositions which include only an unsaturated phospholipid, for example, Egg-phosphatidylcholine, show virtually no effect on the rate of surface-adsorption. The addition of a sterol, for example, cholesterol, to an unsaturated phospholipid has been shown to increase adsorption rate and reduce surface tension marginally. Moreover, where a triglyceride, such as triolein (TO), is added to a mixture of Egg-phosphatidytylcholine and cholesterol, a surprisingly even greater accelerated rate of adsorption and lowering of surface-tension properties occurs.

The method of formulation of the various surfactant-replacement compositions does not appear to be particularly crucial. The surfactant replacement effect can be obtained, for example, by administering the lipids in the form of a colloidal, microemulsion or liposomal suspension of the selected composition in any pharmaceutically acceptable diluent. While virtually any pharmaceutically acceptable aqueous diluent may be employed, such compositions are commonly diluted in physiological saline. For industrial use, the selected composition may be diluted in a number of diluents, for example, water. The methods described for the formulation of lipid compositions in Section III of the specification also apply to the compositions used in the presently proposed surfactant replacement compositions.

The formulation of the subject surfactant replacement compositions resemble microemulsions. As a result, some of the subject compositions deliver surfactant to the surface in question in a more readily transferable mono-layer form. The compositions may also take on a variety of forms, including liposomal, mixed micellar, microemulsion or a mixture of these. However, it is expected that compositions with a proportionately

TABLE VIII

Protective Effect of Lipid Mixtures Against Different Animal (Rat) Models of Experimentally-Induced Gastric Ulcerogenesis[a]

| | Saline | Lipid $PC_e$ + CH + TO | Lipid $PC_e$ + CH + TO + VitC | Lipid DPPC + TP | Lipid DPPCE + TP |
|---|---|---|---|---|---|
| Ethanol (100%) | 100.0 ± 7.2 (22) | 37.5 ± 10.7* (14) | 44.9 ± 15.2* (10) | 23.2 ± 7.6* (19) | 32.3 ± 13.9* (8) |
| Stress (cold-restraint) | 100.0 ± 13.3 (7) | 54.3 ± 15.7* (7) | 29.7 ± 13.2* (8) | 30.0 ± 10.2 (11) | 25.0 ± 8.8* (12) |
| Bile Salt (160 mM taurocholic acid in 0.2 N HCl) | 100.0 ± 15.1 (7) | 17.8 ± 5.7* (7) | 5.8 ± 3.3* (6) | 18.7 ± 11.2* (8) | 47.8 ± 16.2* (7) |
| Aspirin (10 mg/ml, pH 3.0) | 100.0 ± 25.3 (12) | 18.2 ± 18.2* (4) | 27.3 ± 27.3 (4) | 22.2 ± 11.0* (12) | 72.7 ± 36.2 (3) |

[a]All values expressed as % of lesion score of saline-treated control rats. All rats were pretreated with 1 ml of lipid mixtures (5 mg/ml) or saline (controls) 2 hrs before ulcer challenge
( ) = no. of rats/group
* = $p < 0.05$ vs lesion score of saline-treated control rats greater amount of neutral lipids to phospholipids will form a microemulsion or mixed micellar suspension.

The particular form of the lipid composition may affect the rate of phospholipid surface adsorption For example, a liposomal structure would require that the bilayer first be degraded to monolayer form before phospholipid is transferred to a surface, a structural transformation which would not be necessary with a microemulsion. It is thus hypothesized that the particular phospholipid/neutral lipid form may affect rates of surfactant adsorption. There is no requirement that liposomes be made in order to achieve useful compositions in accordance with the present invention. For example, disrupted or aggregated liposomes, or non-liposomal dispersions, appear to be at least as efficient as intact liposomes. It is hypothesized that at the optimal proportion of phospholipid:sterol:triglyceride, the most rapid surface adsorption state would be a microemulsion. However, the actual form of the composition is in other respects the same as that described at Section III, infra of this specification.

For surfactant replacement therapy, a sufficient amount of the suspension composition is administered to adequately cover the desired tissue or alveolar surface. Generally, sufficient coverage is obtained for tracheal instillation to the pulmonary tissue by administering 0.5 ml to 20 ml of a 0.01 to 10 g. lipid/ml. suspension per application. However, as will be appreciated, dosages of the formulations are not known to be particularly limited by any toxicity problems. Further, the lipid mixtures can be administered in a dry state, for example as a dry powder in lyophilized form.

VI. Examples Illustrating Preferred Embodiments of Surfactant Replacement Compositions The following examples are representative experiments which have been included herein to illustrate Applicant's preferred embodiments. One set of experiments was designed to compare the surfactant replacement efficiency of various lipid preparations with triglycerides verses phospholipids alone. A second set of experiments was conducted to compare the surfactant replacement efficiency of various lipid-triglyceride preparations plus a sterol verses lipid-triglyceride preparations alone. The standard technique for measuring surface tension by dynamic compression of the surface fluid in a Langmir Trough was employed to compare the rate and degree of surface-tension lowering and air/liquid interface incorporation of various lipid compositions. Surface-tension and contact angle analysis determinations were made at 10 minutes post-administration of the particular lipid mixture utilizing the system outlined previously.

In the method of surface pressure analysis, a platinum flag is first placed vertically n ultra clean solution at one end of a water bath which is maintained at 37° C. The hydrophilic platinum flat in turn is attached to a force transducer whose output is displayed on a recorder so that the surface tension of the solution can be continuously monitored. In addition, an acid-cleaned glass slide, which is attached to a motorized pulley system, is submerged in the water near the platinum flag. At zero time a liposomal or colloidal suspension of the 20–100 micrograms of the test lipid is applied to the surface of the bath (total bath volume=425 ml, total bath surface area=315 cm$^2$) and a barrier at the far end is advanced at a fixed rate towards the platinum flag, thus compressing the lipid film on the surface of the bath. As the surface film is dynamically compressed, the adjacent amphipathic molecules will tend to form a surface monolayer and the surface tension of the water in the vicinity of the platinum flag will incrementally decrease (Langmuir, (1916) *J. Am. Chem. Soc.*, 38:2221–2295; Noter, Rit, (1984); *Pulmonary Surfactant*).

Through much experimentation, Applicant has found that 24 hours after application of 20–100 micrograms of dipalmitoyl phosphatidylcholine (DPPC) to a bath, surface tension is lowered to a minimal value when the surface area of the bath is compressed to 10% of its original value (90% compression). Thus, the data which is presented below is based on the surface tension of water at a compression of 90%.

In the following studies, the lipid monolayer at the water surface was transferred to the hydrophilic glass slide as the slide was pulled out of the bath using a pulley system when the surface tension reached a minimal value. The slide was then allowed to air dry and then placed on the stage of a goniometer where its surface hydrophobic properties were analyzed by contact analysis. (See FIG. 14).

These experiments provide a model for directly comparing the efficiency of the various surfactant-replacement compositions. In addition, these experiments provide a reasonable basis from which to determine their affect on surface hydrophobic properties of the pulmonary alveolar lining. The correlation between the surfactant replacement and hydrophobicity-creating activities of the compositions therefore becomes readily apparent.

For the following experiments, the same process for the preparation of lipid suspensions outlined at Section IV, pgs. 42–46, were followed.

The contact angle test was employed to compare and illustrate the ability of the lipid composition embodiments to instill hydrophobicity to a treated surface. Surface hydrophobicity is quantified by contact angle analysis on an instrument called a goniometer, where a microliter droplet of water is applied to a surface and the angle at the air/liquid/solid interface is recorded. Hills, et al. (1983) *Am. J. Physiol.* 224:G561–568. The droplets tend to bead up on hydrophobic surfaces resulting in proportionately greater contact angle readings.

The mixtures which were employed in the following experiments were shown by Applicant to be highly effective in lowering surface tension and promoting phospholipid incorporation at an air/liquid interface. The mechanism by which these mixtures potentiated these effects, especially dipalmitoyl phosphatidylcholine (DPPC), was unknown. In an attempt to investigate this mechanism, the following experiments were conducted. These experiments also serve as examples which illustrate the invention, but are not intended to be limitations thereon.

EXAMPLE 1

Comparative studies examining various surface properties were performed after lipid administration in various forms. The surface property effects of a phospholipid colloidal suspension of a triglyceride+dipalmitoyl phosphatidylcholine was compared to a lipsomal suspension of dipalmitoyl phosphatidylcholine alone. Surface tension and contact angle analysis were then assessed after each composition administration.

The two exemplary mixtures comprised (1) dipalmitoyl phosphatidylcholine (DPPC) and (2) dipalmitoyl phosphatidylcholine plus the triglyceride, tripalmitin (DPPC-TP). The DPPC-TP mixture was formulated in a 1:4 parts ratio as a mixed colloidal suspension in a 0.86% NaCl solution in distilled water (pH 7.0, 100 micrograms/ml). The relative amounts of DPPC and tripalmitin in each of the exemplary solutions are showing in Table IX.

TABLE IX

|  | DPPC | TP |
|---|---|---|
| DPPC | 1000 micrograms | — |
| DPPC + TP | 200 micrograms | 800 micrograms |

The above triglyceride and phospholipid amounts were weighed in a screw cap vial and then dissolved in about 5 ml. chloroform. The chloroform was then evaporated under a stream of $N_2$ gas at room temperature. 10 milliliters of a solution of 0.86% NaCl in distilled water (pH 7.0) was then added, which was sufficient to provide a final concentration of 100 micrograms lipid/ml.

The entire admixture was then sonicated for several minutes at temperatures above the transition temperature of the lipids. The suspension thus had a total lipid concentration of 100 micrograms/ml.

While virtually any pharmaceutically acceptable aqueous diluent may be employed, isotonic saline is generally preferred. One milliliter of each of the above suspensions were administered (100 micrograms total lipid) individually as a liposomal/colloidal suspension to the saline contained in a Langmuir Trough. Surface tension was analyzed at varying periods of time after application. Contact angle analysis was also conducted of a slide prepared concurrently with each composition.

(a) Surface Tension Analysis

All data presented is based on the surface tension of saline compressed to 10% of its original value (90% compression). This is because Applicant has learned from previous experimentation that surface tension over the bath is lowered to a minimal value only when the surface area of the bath is thus compressed.

Figure 13:
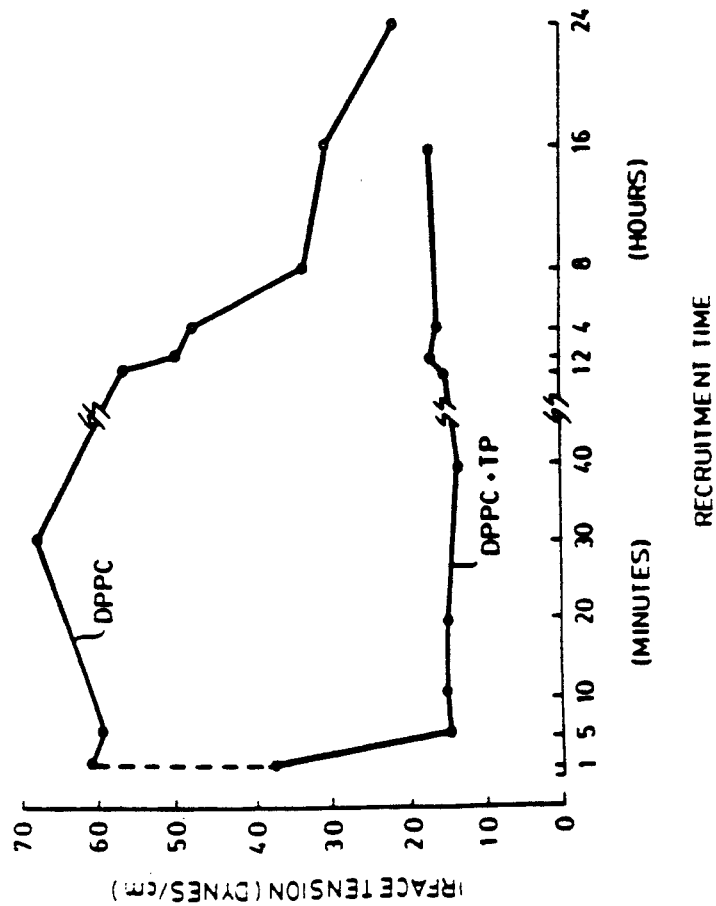
FIG. 13. Effect of neutral lipid on the kinetics of phospholipid-induced lowering of the surface tension. 100 micrograms of total lipid was administered as an aqueous liposomal or colloidal suspension at time zero to a 425 ml saline solution contained in a Langmuir Trough (surface area=315 cm$^2$).

As the results of FIG. 13 demonstrate, DPPC molecules alone spread more slowly and recruited to the air/liquid interface at a much slower rate. The maximal lowering of surface tension occurred at 16-24 hours post-administration (t ½ equalled to 4 hrs). In sharp contrast, the addition of the triglyceride, TP, to the DPPC suspension markedly accelerated the adsorption of the surface-active molecules to the air/liquid interface, with maximal lowering of surface tension occurring within the first 5 minutes post-administration (t ½ equaled to less than 1 minute). Additionally, the maximal surface tension lowering effect induced by the DPPC/TP suspension was significantly lowered by 5-8 dynes/cm than that induced by DPPC alone.

(b) Contact Angle Analysis

Contact angle analysis was performed on the surface of the glass slide obtained from the Langmuir bath after each particular phospholipid composition was tested. Before the lipid suspension was administered to the Langmuir bath, an acid-cleaned glass slide attached to a motorized pulley system was submerged in the saline near an emplaced platinum flag. As will be recalled, the platinum flag was placed vertically in ultra clean water at one end of the water bath. The hydrophilic platinum flag in turn is attached to a force transducer whose output is displayed on a recorder.

At zero time, 1 ml. of microemulsion or colloidal suspension of a 100 micrograms/ml phospholipid composition was applied to the surface of the bath. At various time period thereafter (1 min-24 hrs), a barrier at the far end of the bath was advanced at a fixed rate towards the platinum flag, thus, compressing the lipid film on the surface of the bath. As the surface film was dynamically compressed, the adjacent amphipathic molecules tended to form a surface monolayer and the surface tension of the water in the vicinity of the platinum flag incrementally decreased.

When the surface tension reached a minimal value, the lipid monolayer at the bath surface (air/liquid interface) was transferred to the hydrophilic glass slide as the slide was pulled out of the bath vertically using the previously described pulley system. The slide was then allowed to air dry and then placed on the stage of a goniometer. So emplaced, the hydrophobic properties of the slide surface were determined by contact angle analysis. (See FIG. 14)

Figure 15:
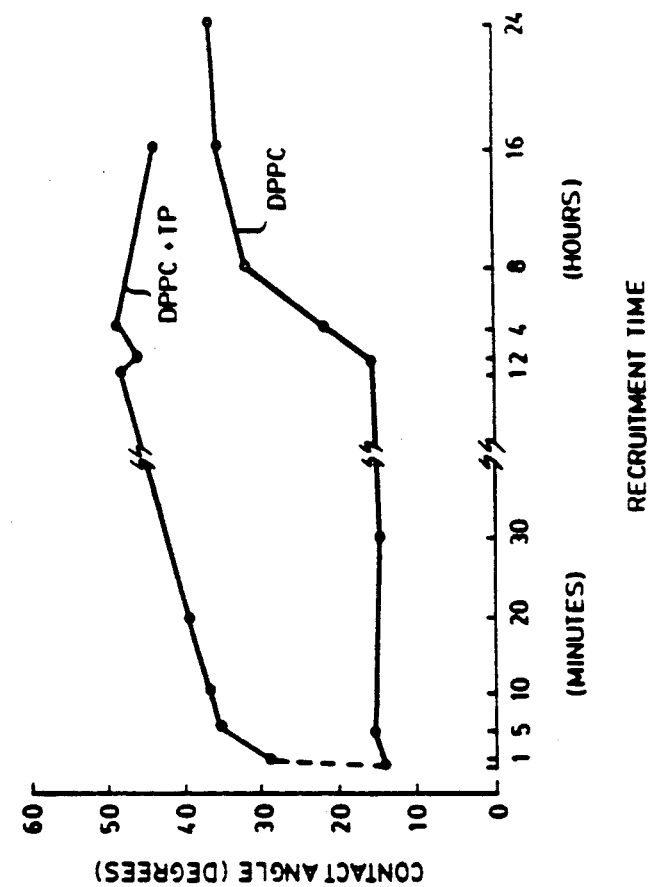
FIG. 15. Effects of neutral lipid on the kinetics of phospholipid-induced enhancement in the surface hydrophobicity (contact angle) of a glass slide. 100 micrograms of the total lipid was administered as an aqueous liposomal or colloidal suspension at time zero.

As will be appreciated from FIG. 15, contact angle analysis of the glass slide surface from the DPPC alone treatment indicted maximal hydrophobic properties of 35°-37° attained at 16-24 hours after DPPC molecules were initially applied to the bath. In contrast, a comparable or greater lipid-induced rise in contact angle was accomplished in less than 10 minutes after application of the DPPC/TP mixture. A maximal contact angle reading of 47°-49° was reached at or before 1 hour post-administration.

These results suggest the addition of a triglyceride, such as tripalmitin to a phospholipid such as dipalmitoyl phosphatidylcholine, will enhance the phospholipid surface activity and markedly accelerate its rate of surface adsorption. Other mixture ratios of DPPC/TP were prepared for comparative studies with the 1:4 mixture of the present invention. The results of these comparative studies are set forth in example 2.

EXAMPLE 2

Comparisons of the effects of various lipid mixtures on surface tension and contact angle hydrophobicity were conducted. The total lipid content per test dose was decreased from 100 micro/ml to 20 micro/ml in these experiments.

In an experiment similar to Example 1, seven different lipid mixtures containing varying ratios of DPPC:TP totalling 20 micro/ml lipid were compared. Surface tension analysis and contact angle hydrophobicity were performed for each mixture as described in Example 1.

The ratios of the particular DPPC:TP mixtures tested were 20:1, 2:1, 1:1, 1:2, 1:3, 1:4 and 1:8. The following Table X lists the various proportions of the lipids in each of these compositions.

TABLE X

|  | RATIO | | | | | | |
|---|---|---|---|---|---|---|---|
|  | 20:1 | 2:1 | 1:1 | 1:2 | 1:3 | 1:4 | 1:8 |
| DPPC micrograms/ml. | 20.0 | 13.3 | 10 | 6.7 | 5 | 4 | 2.5 |
| TP | 0.0 | 6.7 | 10 | 13.3 | 15 | 16 | 17.75 |

Figure 16:
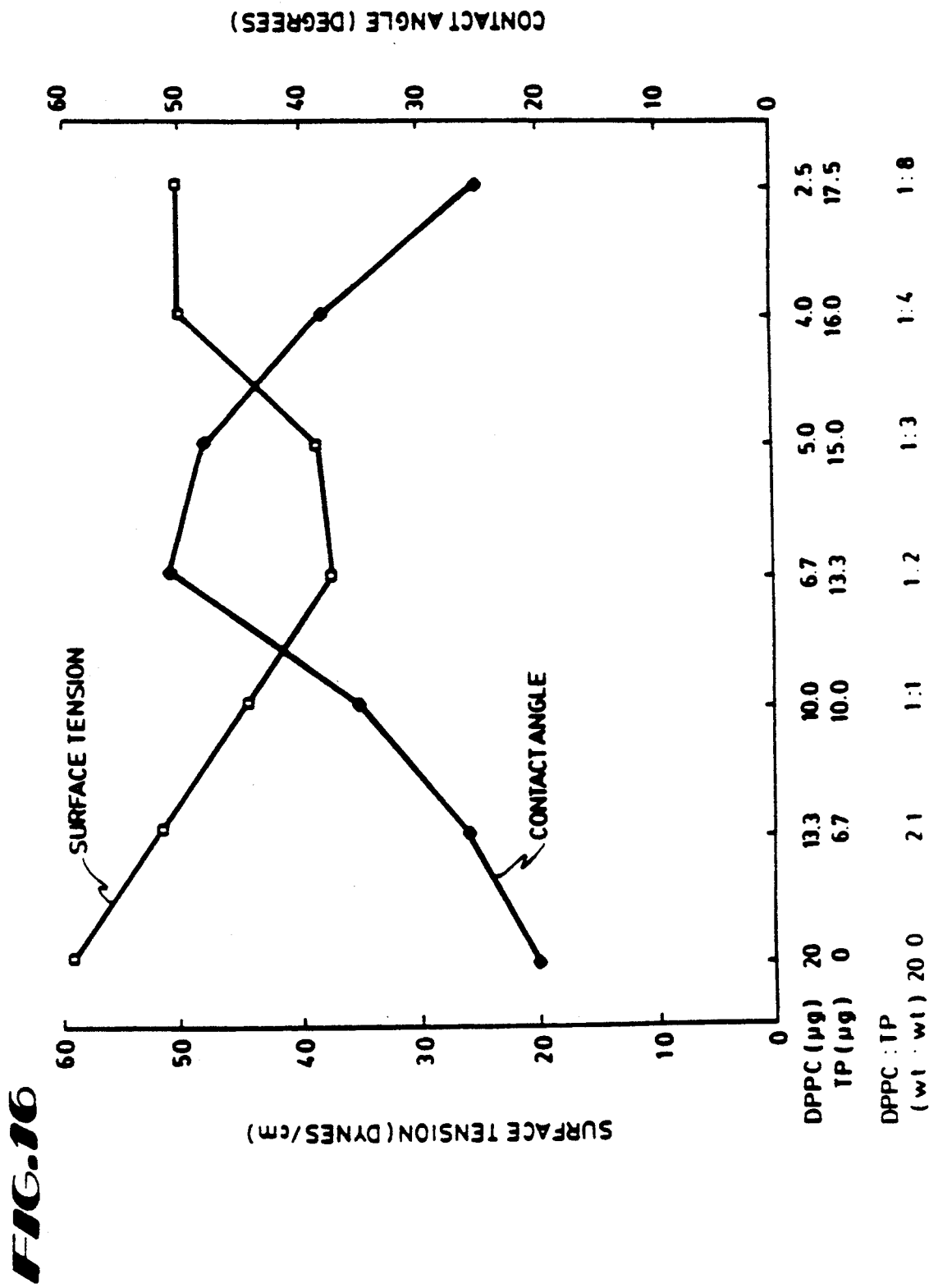
FIG. 16. Importance of the proportions of the ratio of phospholipid (DPPC): neutral lipid (TP) on its catalytic effect on surface adsorption ten minutes post-administration as determined by both surface tension and contact angle analysis as described above. 20 micrograms of total lipid was administered as an aqueous liposomal or colloidal suspension at time zero.

The results, which are documented in FIG. 16, reveal that maximal effects on surface tension lowering were obtained with a unique mixture of DPPC:TP at a ratio of 1:2 (i.e., 6.7 micrograms DPPC; 13.3 micrograms TP). The contact angle results also indicated maximal contact-angle enhancing when the 1:2 ratio of DPPC:TP was applied to the test bath.

This data indicates the specific nature of the 2:1 molecular interaction of neutral to polar lipids.

EXAMPLE 3

Comparisons on the effects of various phospholipid mixtures on surface tension and contact angle were performed. The three compositions studies were (1) Egg phosphatidylcholine (100 micrograms), (2) Egg phosphatidylcholine (PCe)+cholesterol (Chol) and (3) Egg phosphatidylcholine (PCe)+cholesterol (Chol) +triolein (TO). The proportions of each substance in each test composition is shown in Table XI. A total of 100 micrograms total lipid was contained in each test dose.

TABLE XI

|  | PCe | CHOL | TO |
|---|---|---|---|
| PCe | 100 μg | — | — |
| PCe + CHOL | 67 μg | 33 μg | — |
| PCe + CHOL + Triolein | 13.4 μg | 6.6 μg | 80 μg |

Figure 18:
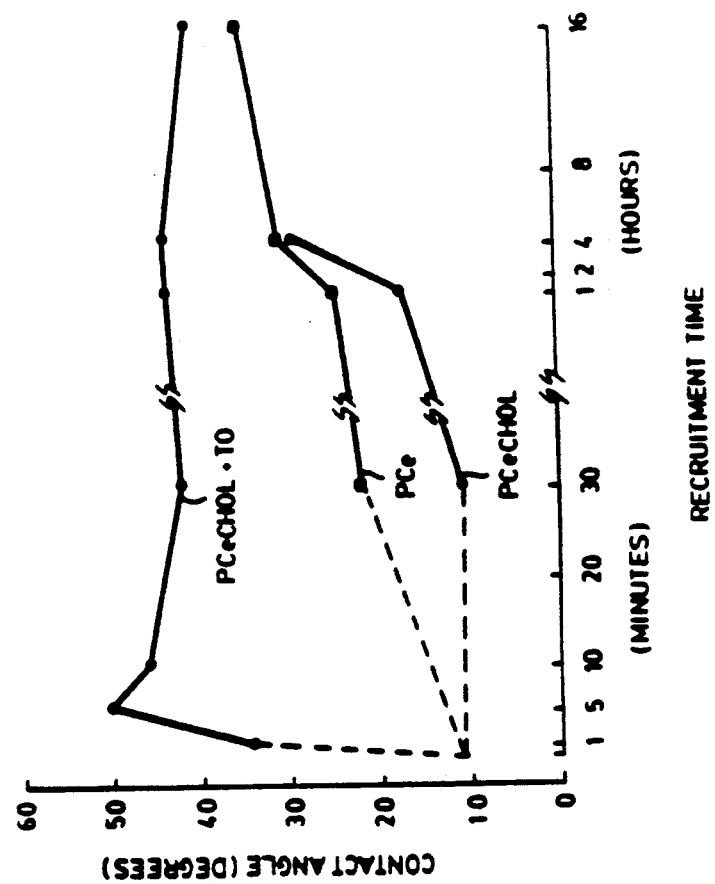
FIG. 18. Effects of neutral lipid (i.e. TO) on the kinetics of enhancement in the surface hydrophobicity (contact angle of a glass slide induced by mixtures of unsaturated phospholipid and sterol ($PC_e$+Chol). 100 micrograms of the total lipid was administered as an aqueous liposomal or colloidal suspension at time zero.
Figure 17:
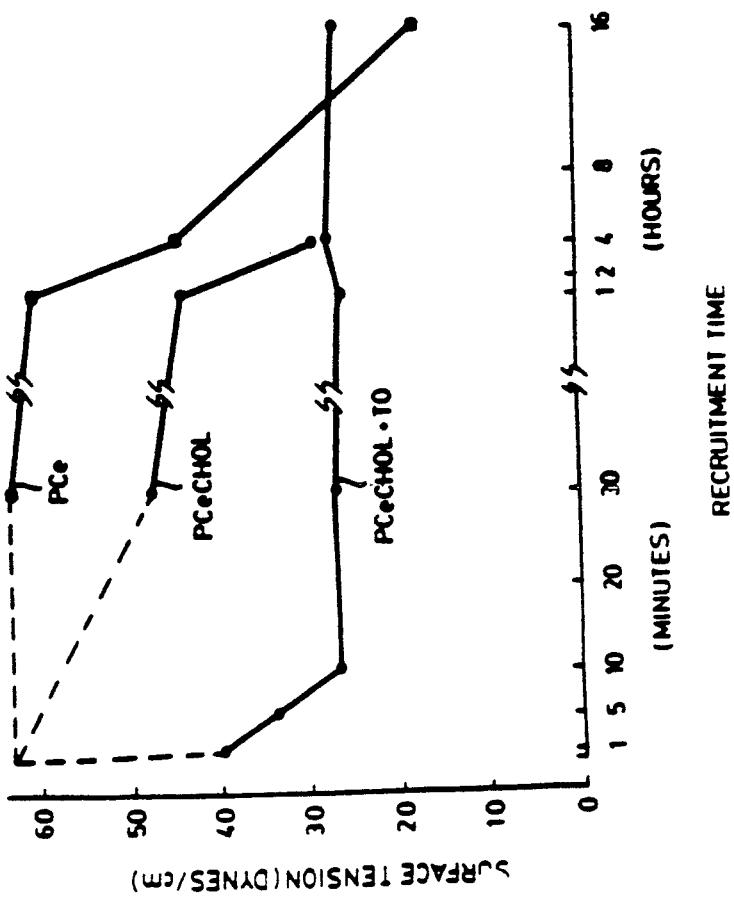
FIG. 17. Effects of neutral lipids on the kinetics of phospholipid-induced lowering of the surface tension of saline. 100 micrograms of total lipid was administered as an aqueous liposomal or colloidal suspension at time zero.

As shown in FIGS. 17 and 18, surface tension was reduced to a minimum value and contact angle raised to a maximal value approximately 16 hours after 100 micrograms of PCe was added to the bath. In contrast, the same amount (100 micrograms) of the PCe+-CHOL+TO mixture induced comparable changes in surface tension and contact angle in 5-10 minutes post-administration.

These results suggest that the addition of an unsaturated triglyceride, such as triolein (TO) to a mixture of an unsaturated phospholipid, such as egg phosphatidylcholine, and a sterol, such as cholesterol, will enhance surface adsorption of the phospholipid as indicated by the surface tension lowering capacity and hydrophobicity increasing capacity of the composition.

The invention is additionally illustrated in connection with the following proposed Examples which are to be considered illustrative of the present invention. It is to be understood, however, that the invention is not limited to the specific details of the examples.

EXAMPLE 4

The following saturated phospholipid and saturated triglyceride was weighed and dissolved in a 5 ml. volume of chloroform. The amount of each component to be weighed is shown in Table XII.

The chloroform is then to be evaporated off under an $N_2$ stream. The final proportions of phospholipid (DPPC) to neutral lipid, tripalmitin (TP), is to be 30% DPPC to 70% tripalmitin (TP).

TABLE XII

| dipalmitoyl-phosphatidylcholine (DPPC) | 10 mg |
|---|---|
| tripalmitin (TP) | 30 mg |

A sufficient volume of isotonic saline was added to the dried lipid residue so as to constitute a concentration of 10 micro/mol lipid phosphorus/ml.

The mixture was then sonicated for 15 minutes at room temperature. The composition was again shaken immediately before intratrachael administration. Particular individual doses of this suspension were calculated according to the formula 150 micro/mol lipid phosphorus/kg. bodyweight of the subject to be treated.

EXAMPLE 5

The following unsaturated phospholipid, egg phosphatidylcholine (PCe), unsaturated triglyceride, trolein (TO), and sterol, cholesterol (Chol), were weighed and dissolved in a 5 ml. volume of chloroform. A mixture of PCe and Chol, 50 M% of each, was first prepared for use in the final composition for intratrachael adminstration. Of this PCe-Chol mixture, 1 mg. was mixed with 4 mg. of triolein (TO). The amount of each component in the composition is shown in Table XIII.

TABLE XIII

| (PCe) + (CHOL) | 1 mg |
|---|---|
| (TO) | 4 mg |

The final proportion of PCe:Chol:TO was a 0.67:0.33:4.0 ratio concentration. The chloroform was then evaporated under $N_2$ and a sufficient volume of isotonic saline was added so as to constitute a concentration of 19 micro/mol lipid phosphorous/ml.

The mixture was then vortexed for 15 minutes at room temperature. The composition was vortexed or otherwise shaken immediately before use. Particular individual doses of this suspension were calculated according to the formula 150 micro/mol lipid phosphorous/kg. body weight of the subject to be treated.

An alternative method of preparing the phospholipid composition is to prepare the colloidal suspensions as described above and then to lyophilize the samples overnight to form a freeze-dried powder. This dry surfactant-neutral lipid mixture can then be blown directly into the lower airway as a dry powder with the use of an endotracheal tube.

EXAMPLE 8

Buoyant Density of Phospholipids Effect of the Addition of a Triglyceride

The present experiment was performed to determine the effect on buoyant density attributable to the addition of a triglyceride to a preparation of saturated phospholipids. The saturated phospholipid used in the current studies was dipalmitoylphosphatidylcholine (DPPC) at a concentration of 1 mg./ml. The saturated phospholipids were prepared as outlined previously. (Specification, beginning at pg. 50, lines 14, through pg. 51, line 3). Preparations of DPPC and the triglyceride, tripalmitin (TP), were also used in the present experiment and prepared in the manner referenced above. The extracted phospholipid was then suspended in either an electrolytic diluent (saline) or non-electrolytic solution (mannitol). All preparations were sonicated for 15 minutes under a nitrogen atmosphere at room temperature before loading into inverted 5 ml. syringes. The concentration of TP used was 4 mg./ml. The four phospholipid preparations outlined in Table XIV were then loaded into the inverted 5 ml. syringes and allowed to settle for 1 hour at room temperature. Four equal fractions were then collected from each of the four preparations. The collected fractions were then stored at −20° C. and assayed for phosphorous.

(a) Phosphorous Assay

The levels of phosphorous in each fraction obtained from each of the tested lipid preparations appears below in Table XIV. A 70% preparation of perchloric acid (0.65 ml) was added to each tube and vortexed. This was heated at 180° C. for 20 minutes, after which time distilled water (3.3 ml) was added. Ammonium molybdate was then added (2.5%–0.05 ml) and vortexed. This mixture was heated for 5 minutes at 100° C. and then centrifuged at 1200 RPM for 10 minutes. The samples were then read on a spectrophotometer at 797 nM and levels read compared to standards tested at the same time. The results indicate that the addition of a triglyceride, such as tripalmitin, to a saturated phospholipid will greatly increase the buoyant density of the phospholipid. The buoyant density was found to be unaffected by the particular diluent used.

TABLE XIV

SETTLING RATES OF PHOSPHOLIPIDS WITH AND WITHOUT TRIGLYCERIDES
P concentration (% of Total Phoephorous)

| | Fraction | | | |
|---|---|---|---|---|
| | (Bottom) 1 | 2 | 3 | (Top) 4 |
| DPPC/Saline | 25.10% | 24.96% | 24.98% | 24.96% |
| DPPC:TP/Saline | 7.79% | 8.42% | 1.91% | 81.88% |
| DPPC:TP/Mannitol | 3.59% | 3.03% | 9.88% | 83.51% |

Fraction 1 was the bottom-most fraction and was collected first from the inverted syringe, and corresponds to the amount of phosphorous which settled out first and thus had the lowest buoyant density. Fraction 4 is the top-most fraction collected last from the inverted syringe, and reflects the amount of phosphorous which did not settle out, and thus has the highest buoyant density.

This data suggests the rapid rate of phospholipid adsorption to an air/liquid interface observed by the addition of a triglyceride to a saturated phospholipid, such as DPPC, may be due to the increased buoyant density imparted to the phospholipid from its association with a triglyceride. Such a TP-associated phospholipid would thus be capable of moving more quickly towards a surface. These characteristics are especially desirable in the formulation of a pulmonary surfactant replacement preparation as the phospholipids would quickly gravitate to and be adsorbed onto the air/liquid interface over the pulmonary alveoli.

This data is also hypothesized to suggest that the actual physical form of the phospholipid TP-composition need not be liposomal and may be more effective and rapid acting in a non-liposomal state. The equal phosphorous distribution in fractions obtained using a DPPC preparation without triglyceride (TP) suggest the phospholipid was present in a liposomal form in the solvent, giving it a lower buoyant density equal to that of the solvent. Phospholipid associated to a surface would thus first require the gravitation of these less-buoyant solvent-filled liposomes to the surface and the disruption of the liposome structure, making the resulting rate of surface phospholipid adsorption much slower. In contrast the DPPC+TP fractions revealed phosphorous concentrated in the uppermost fractions, suggesting the phospholipids associated with the triglyceride were in a liposomal form.

These studies also suggest that the increased rate of phospholipid adsorption by the addition of a triglyceride (TP) to a phospholipid (DPPC) is a phenomena of the greater buoyant density of the phospholipid-containing macromolecule when in association with a triglyceride. DPPC alone in a solvent associates as a classical liposomal structure having a solvent-filled inner core surrounded by a bilayer of phospholipids.

The actual physical association of the phospholipid and the triglyceride is deemed important to this rate of adsorption, and is also believed to lend evidence to the postulate the most rapidly adsorbed phospholipids are those in non-liposomal form. For example, DPPC when sonicated into a liposomal suspension in either an electrolytic (saline) or non-electrolytic (glucose) solvent, is homogeneously distributed at all solvent depths (see Fractions 1–4, Table XIV). This indicates that DPPC was present as stable liposomal suspensions whose buoyant density reflected that of the solvent. In contrast, the addition of a triglyceride to the phospholipid in either an electrolytic or non-electrolytic diluent resulted in the rapid partitioning of the phospholipid to uppermost fraction (Fraction 4) where the air/liquid interface in present.

Thus, the evidence suggests that the most quickly surface-associated phospholipid preparations are in non-liposome form, and are actually in the forms of a microemulsion or a mixed micella suspension. These forms in which a phospholipid monolayer encapsulates a neutral lipid core enables the phospholipid to incorporate to the surface rapidly without first requiring a dissociation of a liposomal bilayer structure to a monolayer.

Further modifications and alternative embodiments of the compositions and methods of the present invention will be apparent to those skilled in the art in view of the foregoing description. Accordingly, this description is to be construed as illustrative only and is for the purpose of teaching those of skill in the art the manner of carrying out. It is understood that the embodiments of the invention herewith shown are to be taken as presently preferred embodiments. For example, equivalent elements or materials may be substituted for those illustrated and described herein. It is intended, therefore, that the following claims be interpreted to embrace all such modifications and changes.

I claim:

1. A method of lung surfactant replacement therapy comprising administering to the lung of an animal in need thereof a therapeutically effective amount of an artificial lung surfactant in a pharmaceutically acceptable diluent to include concentrations of the following:

an unsaturated phospholipid having the chemical structure—

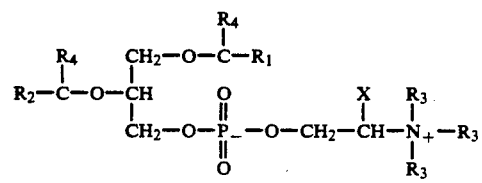

wherein $R_1$ and $R_2$ are unsaturated aliphatic substitutions ranging from 8 to 32 carbon atoms, $R_3$ is H or $CH_3$; X is H or COOH; and $R_4$ is =O or $H_2$;

a sterol having the chemical structure—

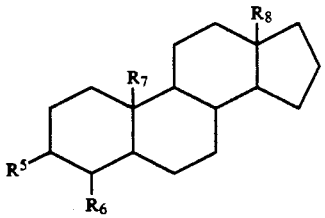

wherein the sterol contains zero, one of multiple double bonds in the perhydrocyclopentanophenanthrene moiety, $R_5$ is either an H,O (ketone) or OH and, $R_6$, $R_7$ and $R_8$ are either H or $CH_3$, and $R_9$ is a straight or branched aliphatic chain of at between 1 and 14 carbon atoms in length;

a triglyceride;

together in a pharmaceutically acceptable diluent, wherein the concentration of sterol and unsaturated phospholipid is less than the concentration of unsaturated neutral lipids.

2. The method of claim 1 wherein the unsaturated phospholipid is egg phosphatidylcholine and the sterol is cholesterol, the composition comprising a weight percent ratio of phospholipid to sterol to triglyceride of about 0.67:0.33:4.0.

3. The method of claim 1 wherein the sterol and triglyceride: unsaturated phospholipid weight ratio is about 1 to about 4.

4. The method of claim 1 wherein the unsaturated phospholipid and neutral lipid are present in mole percent ratios ranging from about 1 to about 4, respectively.

5. The method of claim 1 wherein the unsaturated phospholipid comprises at least one esterified or ether-linked fatty acid selected from the unsaturated fatty acids of Table I.

6. The method of claim 1 wherein the sterol is selected from the group consisting of: cholesterol; desmosterol; B-sitosterol; and campesterol.

7. The method of claim 6 wherein the sterol is $\beta$-sitosterol.

8. The method of claim 1 further comprising a triglyceride having the chemical structure:

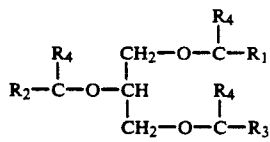

wherein $R_1$, $R_2$ and $R_3$ are each aliphatic substitutions ranging from 4 to 32 carbon atoms; and $R_4$ is either $=O$ or $H_2$.

9. The method of claim 1 wherein the triglyceride is a unsaturated triglyceride and $R_1$, $R_2$ or $R_3$ are saturated aliphatic substitutions.

10. The method of claim 1 wherein the saturated triglyceride comprises at least one esterified or ether-linked fatty acid selected from the saturated fatty acids of Table I.

11. The method of claim 1 wherein the unsaturated phospholipid is dilinoleoyl phosphatidylcholine, the saturated triglyceride is tripalmitin, and the sterol is cholesterol.

12. The method of claim 1 wherein the triglyceride comprises at least one esterified fatty acid selected from the unsaturated fatty acids of Table I.

13. The method of claim 1 wherein the unsaturated phospholipid is egg-phosphatidylcholine and the unsaturated triglyceride is triolein, and the sterol is cholesterol, the composition comprising a weight percent ratio of phospholipid to sterol of about 2:1.

14. The method of claim 1 wherein the weight ratio of unsaturated phospholipid+sterol:unsaturated triglyceride is 1:4.

15. The method of claim 1 wherein the unsaturated phospholipid and the sterol comprise about 20% by weight of the composition.

16. The method of claim 1 wherein the triglycerides comprise about 80% by weight of the composition.

17. The method of claim 1 wherein the pharmaceutically acceptable diluent is selected from the group consisting of:
saline;
glucose; and
water.

18. The method of claim 1 further comprising an effective amount of a non-steroidal anti-inflammatory or antipyretic agent.

19. The method of claim 1 wherein the animal to be treated is identified as having respiratory distress syndrome (RDS).

20. The method of claim 1 wherein the animal is a human.

21. The method of claim 1 wherein the therapeutically effective amount of artificial lung surfactant is a volume sufficient to cover the lung surface to be treated.

22. The method of claim 1 further comprising a pharmaceutically acceptable amount of a polyvalent ion.

23. The method of claim 22 wherein the polyvalent ion is a polyvalent metal ion selected from the group consisting of:
copper;
zinc;
gold; and
aluminum.

24. The method of claim 1 further comprising an effective amount of an antioxidant selected from the group consisting of:
vitamin A;
vitamin E; and
vitamin C.

25. The method of claim 1 wherein the pharmaceutically acceptable diluent is saline.

26. The method of claim 1 further comprising a pharmaceutically acceptable amount of a polyvalent cation selected from the group consisting of:
$Ca++$;
$Bi++$; and
$Al++$.

27. The method of claim 1 further comprising a buffer.

28. The method of claim 1 wherein the composition is administered in a dry-powdered, lyophilized form.

29. A method of accelerating the rate of phospholipid adsorption to an air/liquid interface in an animal in need thereof comprising administering to the alveoler lining an effective amount of a composition of phospholipids and triglycerides.

30. A method of lung surfactant replacement therapy for an animal having neonatal respiratory distress syndrome comprising administering to the lung of an animal having neonatal respiratory distress syndrome a therapeutically effective amount of an artificial lung surfactant in a pharmaceutically acceptable diluent to include concentrations of the following:

an unsaturated phospholipid having the chemical structure—

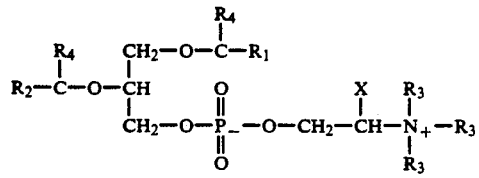

wherein $R_1$ and $R_2$ are unsaturated aliphatic substitutions ranging from 8 to 32 carbon atoms, $R_3$ is H or $CH_3$; X is H or COOH; and $R_4$ is =O or $H_2$;

a sterol having the chemical structure—

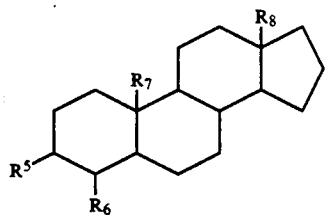

wherein the sterol contains zero, one of multiple double bonds in the perhydrocyclopentanophenanthrene moiety, $R_5$ is either an H,O (ketone) or OH and, $R_6$, $R_7$ and $R_8$ are either H or $CH_3$, and $R_9$ is a straight or branched aliphatic chain of at between 1 and 14 carbon atoms in length;

a triglyceride; together in a pharmaceutically acceptable diluent, wherein the concentration of sterol and unsaturated phospholipid is less than the concentration of unsaturated neutral lipids.

* * * * *

UNITED STATES PATENT AND TRADEMARK OFFICE
CERTIFICATE OF CORRECTION

PATENT NO. : 5,260,284
DATED : November 9, 1993
INVENTOR(S) : Lenard M. Lichtenberger It is certified that error appears in the above-indentified patent and that said Letters Patent is hereby corrected as shown below:

Column 40, claim 1, figure 2, add R9 group to sterol ring at top right--.

Column 44, claim 30, figure 2, add R9 group to sterol ring at top right--.

Signed and Sealed this

Nineteenth Day of July, 1994

Attest:

BRUCE LEHMAN

Attesting Officer     Commissioner of Patents and Trademarks